US010968263B2

(12) United States Patent
Capon

(10) Patent No.: US 10,968,263 B2
(45) Date of Patent: Apr. 6, 2021

(54) AFFINITY SUPPORT AND METHOD FOR TRAPPING SUBSTANCE USING THE SAME

(71) Applicant: Daniel J. Capon, Hillsborough, CA (US)

(72) Inventor: Daniel J. Capon, Hillsborough, CA (US)

(73) Assignee: BIOMOLECULAR HOLDINGS LLC, Burlingame, CA (US)

( * ) Notice: Subject to any disclaimer, the term of this patent is extended or adjusted under 35 U.S.C. 154(b) by 0 days.

(21) Appl. No.: 14/414,329

(22) PCT Filed: Jun. 3, 2013

(86) PCT No.: PCT/US2013/043875
§ 371 (c)(1),
(2) Date: Jan. 12, 2015

(87) PCT Pub. No.: WO2014/014563
PCT Pub. Date: Jan. 23, 2014

(65) Prior Publication Data
US 2015/0197549 A1 Jul. 16, 2015

(30) Foreign Application Priority Data
Jul. 17, 2012 (JP) .............................. JP2012-158647

(51) Int. Cl.
*C07K 14/47* (2006.01)
*G01N 33/543* (2006.01)
(Continued)

(52) U.S. Cl.
CPC .......... *C07K 14/4711* (2013.01); *B01D 15/34* (2013.01); *B01D 15/3804* (2013.01);
(Continued)

(58) Field of Classification Search
CPC .................................................... G01N 33/547
See application file for complete search history.

(56) References Cited

U.S. PATENT DOCUMENTS 5,217,492 A * 6/1993 Guire et al. .................... 600/36
9,725,503 B2 8/2017 Capon
(Continued)

FOREIGN PATENT DOCUMENTS

WO WO 2008/140477 11/2008
WO WO 2012/177775 A1 12/2012
WO WO 2013/065343 5/2013

OTHER PUBLICATIONS

Perdivara et al., "Glycosylation profiles of epitope-specific anti-β-amyloid antibodies revealed by liquid chromatography-mass spectrometry," vol. 19, No. 9, pp. 958-970, published 2009.*
(Continued)

*Primary Examiner* — Tracy Vivlemore
*Assistant Examiner* — Nam P Nguyen
(74) *Attorney, Agent, or Firm* — John P. White

(57) ABSTRACT

Problems to be Solved
The present invention provides an affinity support capable of trapping a substance by cooperative binding that is less likely to cause dissociation even when the substance is a molecule other than an antibody, and a trapping method using the same.
Means to Solve the Problems
A method of trapping a substance comprising the step of contacting an objective to be trapped with an affinity support comprising a support, a spacer bound to the support and an affinity substance bound to the spacer, so as to bind the objective to be trapped to the affinity substance, wherein
(Continued)

each one of the objective to be trapped has a plural of affinity sites and the affinity substance binds to at least two of the affinity sites simultaneously.

5 Claims, 13 Drawing Sheets

(51) Int. Cl.
| | |
|---|---|
| *B01J 20/289* | (2006.01) |
| *B01D 15/38* | (2006.01) |
| *B01J 20/32* | (2006.01) |
| *G01N 33/68* | (2006.01) |
| *H01J 49/00* | (2006.01) |
| *H01J 49/16* | (2006.01) |
| *B01D 15/34* | (2006.01) |

(52) U.S. Cl.
CPC ..... *B01D 15/3809* (2013.01); *B01D 15/3847* (2013.01); *B01J 20/289* (2013.01); *B01J 20/3204* (2013.01); *B01J 20/3208* (2013.01); *B01J 20/3219* (2013.01); *B01J 20/3274* (2013.01); *G01N 33/54353* (2013.01); *G01N 33/6896* (2013.01); *H01J 49/0027* (2013.01); *H01J 49/164* (2013.01); *G01N 2333/4703* (2013.01)

(56) References Cited

U.S. PATENT DOCUMENTS

| | | | | |
|---|---|---|---|---|
| 2004/0265919 | A1* | 12/2004 | Vanderstichele | C07K 16/18 435/7.2 |
| 2005/0027105 | A9 | 2/2005 | Arbogast et al. | |
| 2005/0238641 | A1 | 10/2005 | Burton et al. | |
| 2008/0176340 | A1 | 7/2008 | Soldo et al. | |
| 2008/0254512 | A1 | 10/2008 | Capon | |
| 2009/0252731 | A1 | 10/2009 | Hansen et al. | |
| 2010/0015155 | A1* | 1/2010 | Bales | A61K 47/48215 424/139.1 |
| 2010/0086938 | A1 | 4/2010 | Shimada | |
| 2010/0233678 | A1 | 9/2010 | Beadling | |
| 2011/0046353 | A1 | 2/2011 | Liddell | |
| 2016/0024226 | A1 | 1/2016 | Capon | |
| 2016/0376601 | A1 | 12/2016 | Capon | |
| 2017/0008950 | A1 | 1/2017 | Capon | |
| 2017/0342142 | A1 | 11/2017 | Capon | |

OTHER PUBLICATIONS

Peluso et al., "Optimizing antibody immobilization strategies for the construction of protein microarrays", Analytical Biochemistry, vol. 312, pp. 113-124, published 2003.*

Prasansuklab et al., "Amyloidosis in Alzheimer's Disease: The Toxicity of Amlyoid Beta (Aβ), Mechanisms of Its Accumulation and Implications of Medicinal Plants for Therapy", vol. 2013, Article ID 413808, 10 pages.*

International System of Units, 8th edition 2006.*

Doores et al., Journal of Virology, vol. 84, No. 20, p. 10690-10699, published Oct. 2010.*

Capon et al. "Flexible antibodies with nonprotein hinges", Proc. Jap. Acad., Ser. B 87 (2011) (Year: 2011).*

Kiessling, L. L. et al. (Mar. 24, 2006). Synthetic multivalent ligands as probes of signal transduction. *Angewandte Chemie International Edition in English*, 45(15), 2348-2368.

Notification of Transmittal of the International Search Report and the Written Opinion of the International Searching Authority, or the Declaration, including an International Search Report and Written Opinion of the International Searching Authority, dated Nov. 5, 2013 in connection with PCT International Application No. PCT/US2013/043875, filed Jun. 3, 2013.

English translation of Notification of Reason(s) for Refusal dated Jan. 12, 2016 in connection with Japanese Patent Application No. 2012-158647.

Weimer et al., Influence of a poly-ethylene glycol spacer on antigen capture by immobilized antibodies. J Biochem Biophys Methods Sep. 11, 2000, 45(2), 211-219.

Takacs, M. A., Jacobs, S. J., Bordens, R. M., & Swanson, S. J. (1999). Detection and characterization of antibodies to PEG-IFN-alpha2b using surface plasmon resonance. *Journal of interferon & cytokine research*, 19(7), 781-789.

Soltys, P. J., & Etzel, M. R. (2000). Equilibrium adsorption of LDL and gold immunoconjugates to affinity membranes containing PEG spacers. Biomaterials, 21(1), 37-48.

Shimada T., Toyama, A., Aoki, C., Aoki, Y., Tanaka, K., Sato, T. (2011). Direct antigen detection from immunoprecipitated beads using matrix-assisted laser desorption/ionization time-of-flight mass spectrometry; a new method for immunobeads-mass spectrometry (iMS). *Rapid Commun. Mass Spectrom*, 25, 3521-3526.

* cited by examiner

Fig.4
(A)
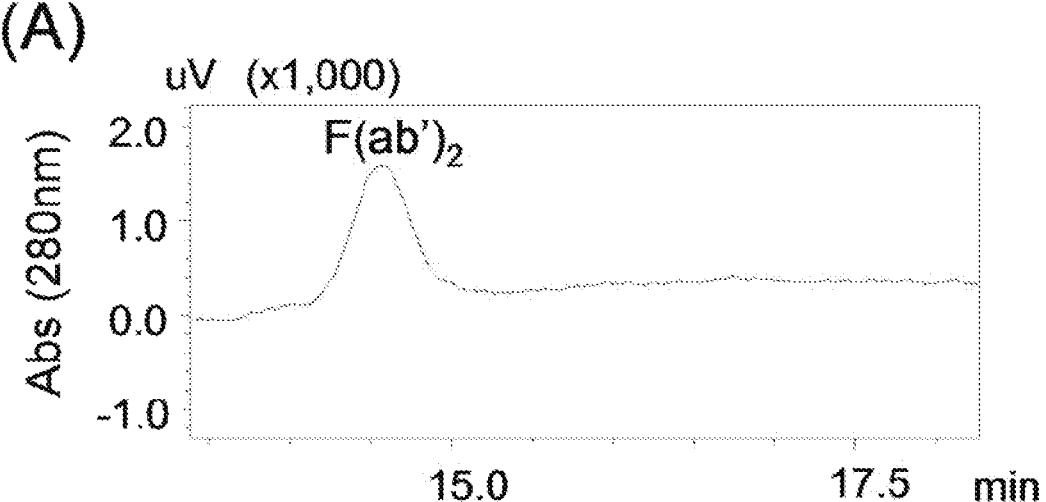
(B)
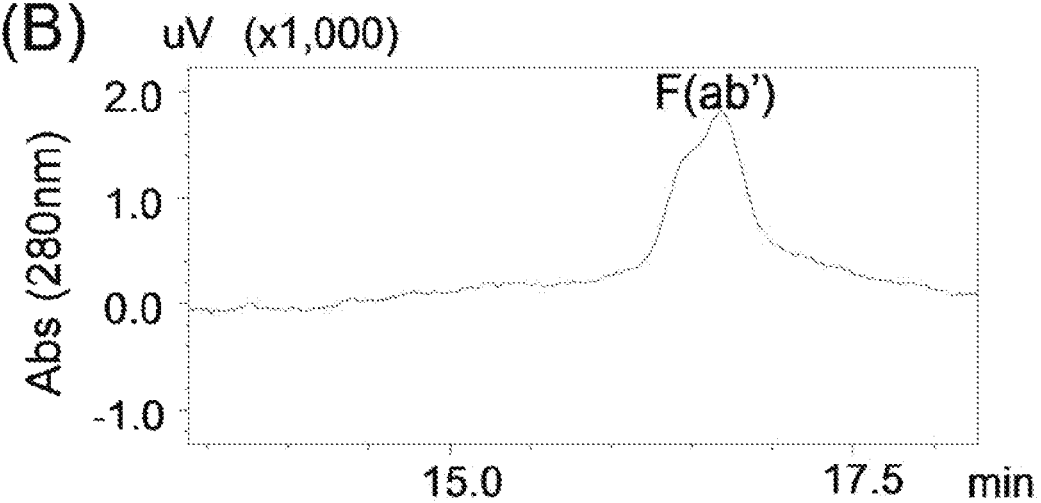

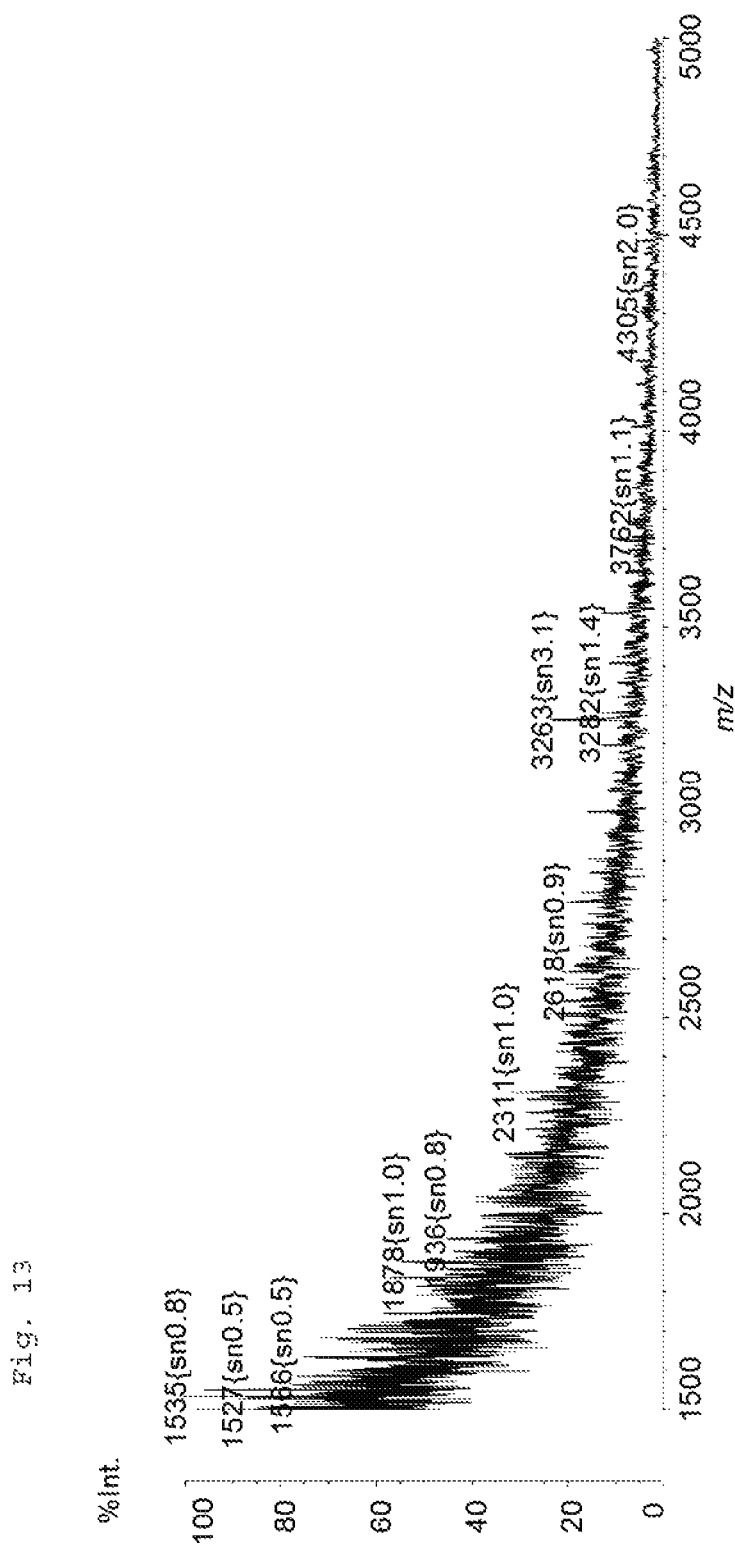

AFFINITY SUPPORT AND METHOD FOR TRAPPING SUBSTANCE USING THE SAME

CROSS-REFERENCE TO RELATED APPLICATIONS

This application is a § 371 national stage of PCT International Application No. PCT/US2013/043875, filed Jun. 3, 2013, claiming priority of Japanese Patent Application No. JP 2012-158647, filed Jul. 17, 2012, the contents of each of which are hereby incorporated by reference in their entirety.

TECHNICAL FIELD OF THE INVENTION

The present invention relates to high-sensitivity measurement and/or structural analysis of molecules contained in a biological sample or the like. The present invention relates to initial diagnosis of diseases, follow-up of diseases, and/or a technique for evaluating chemotherapeutic sensitivity.

BACKGROUND ART

As methods for isolating a specific polypeptide (peptide or protein) from a biological sample such as a cell extract, a tissue extract, or a body fluid (e.g., blood, urine, or spinal fluid), a method using chromatography and a method using molecules having the ability of specific binding, that is, affinity molecules are used.

Examples of the method using chromatography include a method using reverse phase chromatography and a method using ion-exchange chromatography.

Examples of the method using affinity molecules include a method using an affinity support.

For example, Patent Document 1 (JP 7-268000 A) discloses an immune adsorbent composed of a carrier and an antibody bound to the carrier, and describes that the immune adsorbent can be prepared using a polyclonal antibody or a monoclonal antibody as the antibody, and using a crosslinking agent such as N,N'-hexamethylenebismaleimide in order to bind the antibody to the carrier.

Generally, as a method for isolating a target protein from a biological sample, an immunoprecipitation method using protein A/G beads is used. For example, Non-Patent Document 1 (Analytical Biochemistry 1999 Nov. 15; 275(2): 262-5) discloses semiquantitative analysis of amyloid β peptides using a combination of immunoprecipitation and MALDI mass spectrometry.

Further, for example, Non-Patent Document 2 (Proceedings of the Japan Academy, Ser. B, Physical and Biological Sciences 2011; 87(9): 603-16) describes a preparation of a flexible antibody-like molecule composed of an antibody Fc fragment, a hinge region bound to the antibody Fc fragment and having polyethylene glycol, and amyloid β bound to the hinge region.

Non-Patent Document 2 describes that a molecule having two amyloid β peptides (i.e., a two-handed molecule) and a molecule having one amyloid β peptide (i.e., a one-handed molecule) are obtained by the preparation. Further, Non-Patent Document 2 describes that when anti-amyloid β antibody is an objective to be trapped, binding between the two-handed molecule and anti-amyloid β antibody achieves a lower dissociation constant $K_D$ than binding between the one-handed molecule and anti-amyloid β antibody.

It is to be noted that Patent Document 2 (WO2005/037881) describes that a carrier prepared by fixing a ligand to a resin obtained by polymerization of a monomer component having a hydrophilic spacer inserted therein is used to reduce non-specific adsorption to the carrier.

PRIOR ART DOCUMENT

Patent Document

Patent Document 1: JP 7-268000 A
Patent Document 2: WO2005/037881

Non-Patent Document

Non-Patent Document 1: Analytical Biochemistry 1999 Nov. 15; 275(2): 262-5
Non-Patent Document 2: Proceedings of the Japan Academy, Ser. B, Physical and Biological Sciences 2011; 87(9): 603-16

SUMMARY OF THE INVENTION

Problems to be Solved by the Invention

The method using chromatography performs separation and concentration of a target polypeptide in a stepwise fashion using several kinds of carriers, and therefore inevitably requires a large amount of biological sample.

The method using affinity molecules can isolate a target polypeptide in a single treatment due to specific binding achieved by the affinity between molecules, and therefore requires only a minute amount of biological sample. From such a viewpoint, the method using affinity molecules makes up for the shortcomings of the method using chromatography in terms of the amount of a biological sample required. Further, the method using affinity molecules requires less time and is versatile.

However, in the case of the methods using affinity molecules disclosed in Patent Document 1 and Non-Patent Document 1, the collection rate of a target molecule (e.g., a polypeptide) and the amount of incorporated impurities depend on the properties of an affinity carrier (e.g., an immune adsorbent or protein A/G beads). For example, when the affinity carrier is one using an antibody, the efficiency of trapping a target molecule or the amount of non-specifically adsorbed impurities depends on the titer of the antibody. Such limitations inevitably imposed by the properties of the affinity carrier lead to limitations of analytical sensitivity or specificity in mass spectrograph or SDS-PAGE of the target molecule collected by the affinity carrier. Such a problem often results in difficulty in analysis particularly in researches on minute amounts of biomolecules.

The method disclosed in Patent Document 2 is limited to applications using ligands and merely reduces non-specific adsorption, and therefore cannot specifically trap specific target molecules.

In the case of the method using affinity molecules disclosed in Non-Patent Document 2, it is considered that PEG inserted into the hinge region of an antibody provides an appropriate interval between two amyloid peptides (1-15), which makes it possible to simultaneously bind the two amyloid β peptides (1-15) to two F(ab) regions of 6E10, respectively. Thus, it is considered that by binding of one two-handed molecule to one molecule via both two hands of said two-handed molecule (in the present specification, referred to as "cooperative binding"), a binding (with a 100 to 100,000 times lower dissociation constant $K_D$) that is less likely to cause dissociation than binding of one one-handed molecule to one molecule via only one hand of said one-handed molecule is achieved. A binding mode in which one one-handed molecule binds to one molecule via only one hand of said one-handed molecule is the same as that in which a normal antibody binds to an objective to be trapped by the antibody. From such a viewpoint, binding with a low dissociation constant $K_D$, that is, cooperative binding achieved by the method disclosed in Non-Patent Document 2 is expected to make up for the shortcomings of the methods disclosed in Patent Document 1 and Non-Patent Document 1 in terms of the titer of antibody.

However, in the method disclosed in Non-Patent Document 2, the objective to be trapped that can be bound to the antibody-like molecule by cooperative binding is only an antibody molecule (anti-amyloid β antibody molecule (6E10)) similar to the antibody-like molecule in size and shape. That is, Non-Patent Document 2 does not suggest the possibility of achieving cooperative binding between the antibody-like molecule and various molecules other than antibodies, especially polypeptides, which are different in size and shape and may be generally objectives to be trapped by affinity carriers.

A mass spectrometer is a powerful tool for structural analysis of biomolecules. However, in order to perform structural analysis of molecules contained in a biological sample using a mass spectrometer, biomolecules as an objective to be analyzed contained in the biological sample need to be concentrated. This is because a mass spectrometer has a limitation in its detectable level, and therefore an objective to be analyzed in a sample subjected to mass spectrometry needs to be concentrated to a detectable level. In addition to the necessity for concentrating an objective to be analyzed, impurities other than the objective to be analyzed need to be removed. This is because impurities contained in a sample subjected to mass spectrometry cause an increase in the background of data or ion suppression that interferes with the detection of the objective to be analyzed.

It is therefore an object of the present invention to provide an affinity support capable of, even when an objective to be trapped contained in a sample is a molecule other than an antibody, isolating and concentrating the objective by trapping via cooperative binding (i.e., isolating the objective from the sample in a concentrated state) and a trapping method using the same.

Means to Solve the Problems

The present invention includes the following inventions.

(1) An affinity support comprising a support, a spacer bound to the support and an affinity substance bound to the spacer, wherein two to five kinds of the affinity substance bound to the spacer exist in a mixed state.

One specific example of the affinity support according to the above (1) will be described with reference to Example 2.

(2) The affinity support according to the above (1), wherein the length of the spacer is 1 to 100 nm.

(3) The affinity support according to the above (1) or (2), wherein the spacer comprises an oxyalkylene group.

(4) The affinity support according to the above (1) or (2), wherein the spacer is selected from the group consisting of a polyalkylene glycol, a polyoxyalkylated polyol, a polyvinyl alcohol, a polyvinyl alkyl ether, a polysaccharide, a biodegradable polymer, and a lipopolymer.

(5) The affinity support according to any of the above (1) to (4), wherein the spacer is branched, the support is bound to a main chain of the spacer, and the affinity substance is bound to a branched chain of the spacer.

(6) The affinity support according to any of the above (1) to (5), wherein an interval between binding positions on the support of the spacers bound to the affinity substances is 1 to 50 angstrom (Å).

(7) The affinity support according to any of the above (1) to (6), wherein the support is made of a material selected from the group consisting of an agarose, a sepharose, a dextran, a silica gel, a polyacrylamide, a polystyrene, a polyethylene, a polypropylene, a polyester, a polyacrylonitrile, a (meth)acrylic polymer, a fluorocarbon resin, a metal complex resin, a glass, a metal, and a magnetic substance.

The affinity support according to the above, wherein the affinity substance is an amino acid or a peptide having 2 to 50 amino acid residues.

(8) The affinity support according to any of the above (1) to (7), wherein the affinity substance is selected from the group consisting of an immunoglobulin, an immunoglobulin F(ab') fragment, an immunoglobulin F(ab) fragment, an immunoglobulin Fv fragment, a nucleic acid aptamer, a peptide aptamer, a receptor protein, and a bioactive substance.

(9) A method of trapping a substance comprising the step of contacting an objective to be trapped with an affinity support comprising a support, a spacer bound to the support and an affinity substance bound to the spacer, so as to bind the objective to be trapped to the affinity substance, wherein each one of the objective to be trapped has a plural of affinity sites and the affinity substance binds to at least two of the affinity sites simultaneously.

In the present specification, a binding mode in which simultaneous binding of at least two affinity substances to at least two affinity sites (i.e., sites to which affinity substances specifically bind) present in a substance to be trapped is achieved is referred to as cooperative binding. During cooperative binding, it is not required that simultaneous binding to the at least two affinity sites should be always achieved, and for example, there may be a moment when only one of the at least two affinity sites is bound to the affinity substance. That is, cooperative binding is in a state where any one of two or more affinity sites of a substance to be trapped substantially always is bound to an affinity substance so that complete dissociation between the substance to be trapped and the affinity substance is less likely to occur.

The method for trapping a substance according to the above, further comprising the step of washing a surface of the support, to which the affinity substance bound to the substance to be trapped is bound, at a fluid pressure of 0.1 to 200 MPa.

The method for trapping a substance according to the above, wherein a maximum dissociation constant $K_D$ is $10^{-7}$ M.

(10) The method of trapping a substance according to the above (9), wherein one kind of the affinity substance bound to the spacer exists on the affinity support.

One specific example of the method according to the above (10) will be described with reference to Example 1.

(11) The method of trapping a substance according to the above (9), wherein two to five kinds of the affinity substance bound to the spacer exist in the mixed state on the affinity support.

One specific example of the method according to the above (11) will be described with reference to Example 2.

The method for trapping a substance according to the above, wherein the spacer has a length of 1 to 100 nm.

(12) The method of trapping a substance according to any of the above (9) to (11), wherein the spacer comprises an oxyalkylene group.

(13) The method of trapping the substance according to any of the above (9) to (11), wherein the spacer is selected from the group consisting of a polyalkylene glycol, a polyoxyalkylated polyol, a polyvinyl alcohol, a polyvinyl alkyl ether, a polysaccharide, a biodegradable polymer, and a lipopolymer.

The method for trapping a substance according to the above, wherein the spacer is branched, the support is bound to a main chain of the spacer, and the affinity substance is bound to a branched chain of the spacer.

The method for trapping a substance according to the above, wherein an interval between binding positions on the support of the spacers bound to the affinity substances is 1 to 50 angstrom (Å).

The method for trapping a substance according to the above, wherein the support is made of a material selected from the group consisting of an agarose, a sepharose, a dextran, a silica gel, a polyacrylamide, a polystyrene, a polyethylene, a polypropylene, a polyester, a polyacrylonitrile, a (meth)acrylic polymer, a fluorocarbon resin, a metal complex resin, a glass, a metal, and a magnetic substance.

The method for trapping a substance according to the above, wherein the affinity substance is an amino acid or a peptide having 2 to 50 amino acid residues.

The method for trapping a substance according to the above, wherein the affinity substance is selected from the group consisting of an immunoglobulin, an immunoglobulin F(ab') fragment, an immunoglobulin F(ab) fragment, an immunoglobulin Fv fragment, a nucleic acid aptamer, a peptide aptamer, a receptor protein, and a bioactive substance.

(14) The method of trapping a substance according to any of the above (9) to (13), wherein each one of the objective to be trapped is one multimer or one aggregate which comprises a plural of molecules, and each of the plural of the affinity sites exists on each of the plural of the molecules.

(15) The method of trapping a substance according to any of the above (9) and (11) to (13), wherein each one of the objective to be trapped is one molecule.

(16) The method of trapping a substance according to any of the above (9) to (15), wherein the objective to be trapped is a biological substance or a non-biological substance.

(17) The method of trapping a substance according to the above (16), wherein the biological substance is selected from the group consisting of a biomarker, a biomarker candidate molecule, and a fragment generated from a biomarker or a biomarker candidate molecule by splicing.

(18) The method of trapping a substance according to the above (17), wherein the biomarker is related to a disease selected from the group consisting of cancer, brain disease, heart disease, immune disease, hepatic disease, renal disease, and eye disease.

(19) The method of trapping a substance according to the above (16), wherein the biological substance is a virus or a bacterium.

(20) The method of trapping a substance according to the above (16), wherein the non-biological substance is an environmentally hazardous substance.

A method of micro mass spectrometry comprising the steps of:

binding an objective to be trapped to an affinity support by the above method for trapping a substance;

eluting the objective bound to the affinity support from the affinity support; and subjecting the eluted objective to mass spectrometry.

EMBODIMENTS OF THE INVENTION

The present invention provides an affinity support comprising a support, a spacer bound to the support and an affinity substance bound to the spacer, wherein two to five kinds of the affinity substance bound to the spacer exist in a mixed state.

In some embodiments, the length of the spacer is 1 to 100 nm.

In some embodiments, the spacer comprises an oxyalkylene group.

In some embodiments, the spacer is selected from the group consisting of a polyalkylene glycol, a polyoxyalkylated polyol, a polyvinyl alcohol, a polyvinyl alkyl ether, a polysaccharide, a biodegradable polymer, and a lipopolymer.

In some embodiments, the spacer is branched, the support is bound to a main chain of the spacer, and the affinity substance is bound to a branched chain of the spacer.

In some embodiments, an interval between binding positions on the support of the spacers bound to the affinity substances is 1 to 50 angstrom (Å).

In some embodiments, the support is made of a material selected from the group consisting of an agarose, a sepharose, a dextran, a silica gel, a polyacrylamide, a polystyrene, a polyethylene, a polypropylene, a polyester, a polyacrylonitrile, a (meth)acrylic polymer, a fluorocarbon resin, a metal complex resin, a glass, a metal, and a magnetic substance.

In some embodiments, the affinity substance is selected from the group consisting of an immunoglobulin, an immunoglobulin F(ab') fragment, an immunoglobulin F(ab) fragment, an immunoglobulin Fv fragment, a nucleic acid aptamer, a peptide aptamer, a receptor protein, and a bioactive substance.

The present invention provides a method of trapping a substance comprising the step of contacting an objective to be trapped with an affinity support comprising a support, a spacer bound to the support and an affinity substance bound to the spacer, so as to bind the objective to be trapped to the affinity substance, wherein each one of the objective to be trapped has a plural of affinity sites and the affinity substance binds to at least two of the affinity sites simultaneously.

In some embodiments, one kind of the affinity substance bound to the spacer exists on the affinity support.

In some embodiments, two to five kinds of the affinity substance bound to the spacer exist in the mixed state on the affinity support.

In some embodiments, the spacer comprises an oxyalkylene group.

In some embodiments, the spacer is selected from the group consisting of a polyalkylene glycol, a polyoxyalkylated polyol, a polyvinyl alcohol, a polyvinyl alkyl ether, a polysaccharide, a biodegradable polymer, and a lipopolymer.

In some embodiments, each one of the objective to be trapped is one multimer or one aggregate which comprises a plural of molecules, and each of the plural of the affinity sites exists on each of the plural of the molecules.

In some embodiments, each one of the objective to be trapped is one molecule.

In some embodiments, the objective to be trapped is a biological substance or a non-biological substance.

In some embodiments, the biological substance is selected from the group consisting of a biomarker, a biomarker candidate molecule, and a fragment generated from a biomarker or a biomarker candidate molecule by splicing.

In some embodiments, the biomarker is related to a disease selected from the group consisting of cancer, brain disease, heart disease, immune disease, hepatic disease, renal disease, and eye disease.

In some embodiments, the biological substance is a virus or a bacterium.

In some embodiments, the non-biological substance is an environmentally hazardous substance.

Effect of the Invention

According to the present invention, it is possible to provide an affinity support capable of trapping a substance by cooperative binding that is less likely to cause dissociation even when the substance is a molecule other than an antibody, and a trapping method using the same.

The affinity support according to the present invention achieves a 100 to 100,000 times lower dissociation constant $K_D$ than a conventional affinity support. Therefore, the use of the affinity support according to the present invention makes it possible to more efficiently isolate and concentrate a target molecule in a sample (i.e., to bind a target molecule to the affinity support to isolate them from a sample in a concentrated state) as compared to the use of the conventional affinity support. For example, a trapping rate about 5.6 to 8.5 times (molar basis) higher than that of a conventional immunoprecipitation method is achieved, and the sensitivity of analysis of a trapped substance by a mass spectrometer is improved 10-fold. Further, the low dissociation constant $K_D$ makes it possible to expand washing conditions and/or reduce non-specific adsorption.

BRIEF DESCRIPTION OF THE DRAWINGS

FIGS. 4A and 4B are size exclusion chromatograms of a 6E10 F(ab')$_2$ fraction before (FIG. 4A) and after (FIG. 4B) reduction treatment to determine the generation of 6E10 F(ab') fragments by the reduction treatment.

FIG. 13 shows a mass spectrum obtained when 1 pg (307 amol) of amyloid β (1-28) spiked in human plasma was trapped using an affinity support (6E10/4G8 F(ab')-PEG$_{24}$ beads).

MODE FOR CARRYING OUT THE INVENTION

1. Affinity Support

Figure 1:
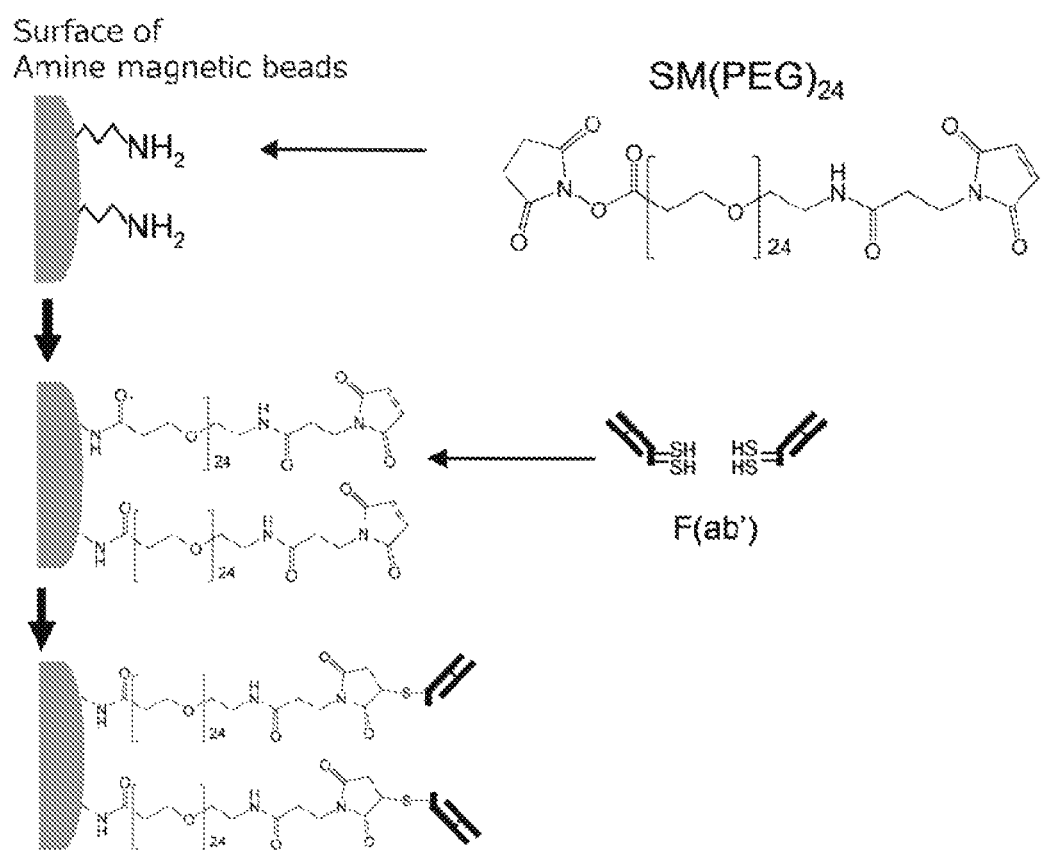
FIG. 1 is a schematic diagram showing a method for producing F(ab')-PEG beads that is one embodiment of an affinity support according to the present invention.

An affinity support according to the present invention comprises a support, a spacer bound to the support, and an affinity substance bound to the spacer. The term "bound" includes direct binding and indirect binding.

1-1. Support

The material of the support may be selected from the group consisting of an agarose, a sepharose, a dextran, a silica gel, a polyacrylamide, a polystyrene, a polyethylene, a polypropylene, a polyester, a polyacrylonitrile, a (meth) acrylic polymer, a fluorocarbon resin, a metal complex resin, a glass, a metal, and a magnetic substance.

The support may have any shape such as a planar shape, a spherical shape, or the like. For example, the support may constitute a chip, a bead, or a flow channel wall in a microdevice for use in separation and/or concentration of a target substance.

1-2. Spacer

It is preferred that one of the ends of the spacer is bound to the support and the other end is bound to the affinity substance. The spacer can play a role in keeping an appropriate interval between the support and the affinity substance, and in imparting flexibility, or both of flexibility and extensibility to said spacer itself to achieve cooperative binding. The spacer preferably has a chain-like (spacer chain) structure. The presence of the chain-like spacer reduces steric hindrance at the support when an objective to be trapped binds to the affinity substance as compared to when the chain-like spacer is not present. As a result, it is possible to enhance the binding strength between the affinity substance and the objective to be trapped.

The length of the spacer is, for example, 1 to 100 nm, preferably 1 to 20 nm, more preferably 5 to 10 nm. When the length of the spacer is less than the above lower limit, the spacer is too short and therefore reach of said spacer is not enough to simultaneously bind two or more affinity substances to two or more affinity sites of an objective to be trapped so that cooperative binding is less likely to occur. When the length of the spacer exceeds the above upper limit, the spacer is too long and therefore the degree of freedom of movable range of the affinity substance is contrarily limited so that cooperative binding is less likely to occur.

The spacer may be, for example, a high molecular weight polymer. The high molecular weight polymer used as the spacer in the present invention usually has a chain-like structure.

The spacer is preferably non-peptidic. The term "non-peptidic" means having no peptide binding.

For example, the non-peptidic spacer may contain an oxyalkylene group. An oxyalkylene group-containing group is a divalent group, and may be, for example, one having 2 to 6 carbon atoms. More specifically, an oxyalkylene in the oxyalkylene group-containing group is ethylene oxide or propylene oxide. The oxyalkylene group-containing group is preferably an organic high molecular weight polymer, that is, a polyoxyalkylene group-containing group. The polyoxyalkylene group-containing group is preferably a polyalkylene glycol group obtained by polymerization of an alkylene glycol having 2 to 6 carbon atoms (e.g., polymerization degree: 2 to 40). For example, the polyalkylene glycol group may be selected from the group consisting of polyethylene glycol group (obtained by polymerization of ethylene glycol), and polypropylene glycol group (obtained by polymerization of 1,2-propanediol or 1,3-propanediol).

In the present invention, particularly, an ethylene glycol group or a polyethylene glycol group having a polymerization degree of 2 to 40, preferably 12 to 36 may be selected as the oxyalkylene group-containing group.

Alternatively, the non-peptidic spacer may be, for example, an organic high molecular weight polymer selected from the group consisting of a polyoxyalkylated polyol, a polyvinyl alcohol, a polyvinyl alkyl ether, a polysaccharide, a biodegradable polymer, and a lipopolymer. An alkyl group in the polyoxyalkylated polyol or the polyvinyl alkyl ether may have, for example, 1 to 6 carbon atoms, preferably 1 to 3 carbon atoms. Examples of the polysaccharide include a dextran, a mucopolysaccharide, and a chitin. Examples of the mucopolysaccharide include hyaluronic acid. Examples of the biodegradable polymer include PLA (poly(lactic acid)) and PLGA (poly(lactic-glycolic acid)).

These organic high molecular weight polymers may have a polymerization degree of, for example, 2 to 40, preferably 12 to 36.

According to one embodiment of the present invention (more specifically, an embodiment in which two or more kinds of the affinity substances are bound to the support in a mixed state), the spacer may be a polypeptide. In the present specification, the term "polypeptide" is used as a generic name for peptides (having, for example, 2 or more and 100 or less amino acid residues) and proteins (having, for example, more than 100 amino acid residues). The polypeptide as the spacer may be a ligand having an affinity for a constant region. Examples of such a ligand include protein A and protein G.

The spacer used in the present invention may be one containing one of the above-mentioned examples or one containing any two or more selected from the above-mentioned examples.

The spacer may be straight chain or branched chain. When the spacer is branched, the support is bound to the end of one of chains, that is, a main chain, and the affinity substance is bound to the end of the other chain, that is, a branched chain. The number of branched chains is not particularly limited, and may be, for example, 2 to 10. When the spacer is branched, the density of the affinity substance on the affinity support can be increased as compared to when the spacer is straight chain.

1-3. Affinity Substance

The affinity substance may be either a guest substance or a host substance that can generally construct a molecular recognition system and can interact by non-covalent bonding. The affinity substance is preferably a host substance.

In the present invention, interaction in molecular recognition means that the affinity substance recognizes and non-covalently interacts with an affinity site of an objective to be trapped, and may be, for example, specific binding with such an affinity that an association rate constant ka (unit: 1/Ms) of at least $10^3$ or $10^4$, for example, $10^3$ to $10^5$ or $10^4$ to $10^5$ is achieved. The number of specific binding sites per one affinity substance may be one or two or more (e.g., five or less).

The affinity substance may or may not have a naturally-derived structure.

Examples of the affinity substance include amino acids and polypeptides. More specifically, the affinity substance may be an amino acid or a polypeptide having 2 to 50 amino acid residues.

Another example of the affinity substance is one selected from the group consisting of an immunoglobulin and an immunoglobulin fragment. The immunoglobulin fragment is not particularly limited as long as it has the ability to bind to antigen, and can be selected from, for example, the group consisting of $F(ab')_2$, F(ab'), Fab, Fd, Fv, L-chain, and H-chain. Among them, from the viewpoint of reducing non-specific adsorption, the immunoglobulin fragment is preferably selected from the group consisting of an immunoglobulin F(ab') fragment, an immunoglobulin F(ab) fragment, and a Fv fragment which have no Fc region. Examples of the immunoglobulin include IgG1, IgG2, IgG3, IgG4, and the like. The immunoglobulin may be derived from any animal, but is particularly derived from a human.

Another example of the affinity substance is one selected from the group consisting of a nucleic acid aptamer, a peptide aptamer, a receptor protein, and a bioactive substance. Examples of the bioactive substance include cytokine, hormones, and neurotransmitters.

The interval between binding positions on the support of the spacers bound to the affinity substances is not particularly limited, and can be appropriately determined by those skilled in the art so that the affinity substances are preferably present as dense as possible. More specifically, the interval between the affinity substance-binding positions may vary depending on, for example, the size of the affinity substance, but is, for example, 1 to 1,000 angstrom (Å), preferably 1 to 100 angstrom, more preferably 1 to 50 angstrom, even more preferably 1.5 to 30 angstrom. The above lower limit substantially corresponds to the physical limit of the interval between adjacent affinity substances. On the other hand, if the interval between the affinity substance-binding positions exceeds the above upper limit, the affinity substances are sparse and therefore cooperative binding is less likely to occur.

According to one embodiment of the present invention, one kind of the affinity substance bound to the support via the spacer is present on the support (more specifically, in a specific region on the support).

According to another embodiment of the present invention, two or more kinds of the affinity substances bound to the support via the spacer are present on the support (more specifically, in a specific region on the support). The number of kinds of the affinity substances used in this embodiment is two or more, but is smaller than, for example, the number of kinds of antibodies constituting a common polyclonal antibody. The amounts of two to five kinds of the affinity substances are preferably the same or close to each other. More specifically, two to five kinds of the affinity substances can be used in such a manner that the difference in amount between arbitrary two kinds of the affinity substances selected from the two to five kinds of affinity substances is within 20%, preferably within 10%, more preferably within 5% (molar basis). Further, in this embodiment, different kinds of the affinity substances are present on the same support in a mixed state. The embodiment in which different kinds of the affinity substances are present on the same support in a mixed state is clearly distinguished from an embodiment in which different kinds of the affinity substances are bound in a state where they can be differentiated from each other (e.g., a microarray).

Treatment may be performed on the specific region on the support depending on the kind of affinity substance bound thereto or the combination of different kinds of the affinity substances bound thereto. Two or more regions may be provided on the same support in such a manner that the kind of affinity substance bound thereto or the combination of different kinds of the affinity substances bound thereto varies from region to region. In this case, different treatments can be performed on the different regions on the same support.

2. Preparation of Affinity Support

The affinity support according to the present invention can be prepared by binding a support having a binding functional group on surface of said support to an affinity substance having a binding functional group via a spacer substance having both a binding functional group corresponding to the binding functional group of the support and a binding functional group corresponding to the binding functional group of the affinity substance simultaneously (i.e., a bifunctional spacer substance) or successively (i.e., a monofunctional spacer substance).

The binding functional group of each of the components, namely, the support, the spacer substance, and the affinity substance, may be selected from the group consisting of covalent binding functional group, ion binding functional group, and hydrogen binding functional group. Particularly, a covalent binding functional group is preferred.

A combination of binding functional groups of the components corresponding to each other can be easily determined by those skilled in the art so that binding selected from the group consisting of covalent binding, ion binding, and hydrogen binding, preferably covalent binding can be achieved.

For example, when the binding functional group of one of the components is an amino group, examples of the binding functional group of the corresponding other component include a carboxyl group, an active ester group (e.g., an N-hydroxysuccinimide (NHS) ester group, and an N-hydroxysulfosuccinimide (Sulfo-NHS) ester group), an epoxy group, an aldehyde group, an isocyanato group, an isothiocyanato group, and the like. When the binding functional group of one of the components is a thiol group, examples of the binding functional group of the corresponding other component include a maleimide group, a pyridyldisulfide group, a vinylsulfone group, a bromoacetyl group, and the like. When the binding functional group of one of the components is a hydroxyl group, examples of the binding functional group of the corresponding other component include an epoxy group, a silyl chloride group, and the like.

The support having a binding functional group on a surface of said support can be prepared by a self-organizing surface method in which molecules having a binding functional group are arranged on the surface of a support; a method in which the surface of a support is coated with a substance having a binding functional group; a method in which a substance having a binding functional group and a functional group that can covalently bind to a support is covalently bound to the surface of the support; or the like. Among these methods, the support having a binding functional group on a surface of said support is preferably prepared by the method based on covalent binding. Among the above-mentioned examples of the binding functional group, an amino group is particularly preferred as the binding functional group of the support.

The density of the binding functional group on the support is, for example, 0.001 to 0.5 mmol/m$^2$, preferably 0.01 to 0.1 mmol/m$^2$.

Each of the binding functional groups of the spacer substance may be one that is naturally present in a biomolecule, one that an organic high molecular weight polymer previously has, or one that is artificially produced by decomposition, synthesis, or modification. A method for producing the binding functional group can be easily selected by those skilled in the art. The binding functional group of the spacer substance corresponding to the binding functional group of the support and the binding functional group of the spacer substance corresponding to the binding functional group of the affinity substance may be the same or different from each other. Among the above-mentioned examples of the binding functional group, a particularly preferred example of a combination of the binding functional groups of the spacer substance is a combination of an active ester group and a maleimide group.

The binding functional group of the affinity substance may be one that is naturally present in a naturally-derived structure or one that is artificially produced by decomposition, synthesis, or modification. That is, the affinity substance having a binding functional group is prepared by a method appropriately selected by those skilled in the art from, for example, isolation from the living body of an organism, decomposition of an isolate from a living body, synthesis by genetic engineering, biochemical synthesis and modification, and organic chemical synthesis and modification. Among the above-mentioned examples of the binding functional group, a thiol group is particularly preferred as the binding functional group of the affinity substance. For example, when the affinity substance is an immunoglobulin fragment, the immunoglobulin fragment can be prepared by digestion using an enzyme (e.g., papain, pepsin, ficin, or the like), and/or by cleavage of disulfide bonds using a reducing agent.

The order in which the respective components are bound to one another is not particularly limited. Therefore, binding between the spacer substance and the affinity substance may be achieved after the support and the spacer substance are bound to each other, or binding between the spacer substance and the support may be achieved after the affinity substance and the spacer substance are bound to each other. When the respective components are successively bound to one another in this way, the spacer substance may be either monofunctional or bifunctional. When a monofunctional spacer substance is used as the spacer substance, the respective components may be bound to one another by, for example, binding the support having a binding functional group to the monofunctional spacer substance having a binding functional group corresponding to the binding functional group of the support, and then producing a binding functional group of the spacer substance corresponding to a binding functional group of the affinity substance, and then binding the spacer substance to the affinity substance via the produced binding functional group.

On the other hand, the respective components may be bound to one another simultaneously by using a bifunctional spacer substance as the spacer substance and subjecting the support, the bifunctional spacer substance, and the affinity substance to the same reaction system.

Further, the respective components are used in such amounts that the affinity substance is bound as dense as possible. More specifically, the spacer substance can be used in an amount 10 to 5,000 times (molar basis) the amount of the binding functional group present in a region on the support where the affinity substance is to be bound, and the affinity substance can be used in an amount 0.1 to 10 times (molar basis) the amount of the binding functional group present in a region on the support where the affinity substance is to be bound.

3. Use of Affinity Support

The affinity support according to the present invention can be used by subjecting said affinity support to a molecular recognition system selected by those skilled in the art depending on the affinity substance bound thereto. More specifically, a sample containing a substance to be trapped is brought into contact with the affinity support to bind the substance to be trapped contained in the sample to the affinity substance on the affinity support.

3-1. Objective to be Trapped and Cooperative Binding

According to one embodiment of the present invention, one objective to be trapped is a single molecule. According to another embodiment of the present invention, one objective to be trapped is one dimer or higher-order multimer composed of two or more molecules or one aggregate.

In one objective to be trapped, two or more affinity sites, that is, sites that specifically bind to the affinity substance(s) are present. The use of the affinity support according to the present invention makes it possible to simultaneously bind at least two affinity substances to at least two of the two or more affinity sites present in one objective to be trapped (i.e., to achieve cooperative binding). During cooperative binding, it is not required that simultaneous binding to the at least two affinity sites should be always achieved. For example, there may be a moment when only one of the at least two affinity sites is bound to the affinity substance. That is, cooperative binding allows any one of the two or more affinity sites of the substance to be trapped to be always bound to the affinity substance, which makes it easy to keep a state where the substance to be trapped is trapped by the affinity substance. In other words, complete dissociation between the substance to be trapped and the affinity substance is less likely to occur.

According to the present invention, as described above in 1-3, the association rate constant ka (unit: 1/Ms) for binding of the affinity substance is comparable to the association rate constant ka of a conventional common molecular recognition system. On the other hand, the dissociation rate constant kd (unit: 1/s) for binding of the affinity substance is lower than that for the conventional common molecular recognition system. Therefore, according to the present invention, the dissociation constant KD (unit: M) for binding of the affinity substance is smaller than that for the conventional common molecular recognition system, and is, for example, $10^{-7}$, $10^{-8}$, $10^{-9}$, $10^{-10}$, $10^{-11}$, or $10^{-12}$ at the maximum and may be, for example, $10^{-13}$ to $10^{-7}$.

For example, when one objective to be trapped is a single molecule, two or more affinity sites are present in the single molecule. In this case, the two or more affinity sites present in the single molecule are generally different from each other. Therefore, two or more different kinds of the affinity substances need to be bound to the affinity support so that the affinity substances can bind to at least two affinity sites simultaneously.

When one objective to be trapped is composed of two or more molecules, at least one affinity site needs to be present in each of the molecules. In this case, two or more molecules constituting one objective to be trapped are generally the same, and therefore have the same at least one affinity site. Therefore, one kind of the affinity substance is bound to the affinity support. However, in this case, the possibility that two or more kinds of the affinity substances are bound to the affinity support is not particularly excluded.

3-2. Sample Containing Objective to be Trapped

An objective to be trapped by the affinity support according to the present invention can be easily determined by those skilled in the art depending on the kind of affinity substance bound thereto or the combination of different kinds of the affinity substances bound thereto.

The objective to be trapped may or may not have a naturally-derived structure.

Specific examples of the objective to be trapped include biological substances, especially polypeptides, sugar chains, nucleic acids, and conjugates of two or more of them (e.g., conjugates obtained by arbitrarily combining two or more of them such as glycopeptides and peptide nucleic acids). These biological substances may have a molecular weight of, for example, 200 to 1,000,000, preferably 1,000 to 200,000.

A more specific example of the objective to be trapped is a biological substance selected from the group consisting of a biomarker, a biomarker candidate molecule, and a fragment generated from a biomarker or a biomarker candidate molecule by splicing. Further, the biomarker may be one related to a disease selected from the group consisting of cancer, brain disease (e.g., Alzheimer's disease), heart disease, immune disease, hepatic disease, renal disease, and eye disease. When the objective to be trapped is such a biological substance, initial diagnosis of diseases, follow-up of diseases, and/or evaluation of sensitivity of chemotherapy for diseases can be performed by the present invention.

Another more specific example of the objective to be trapped is a virus. In this case, the affinity support can trap the surface antigen of a virus. The affinity support according to one embodiment of the present invention having two to five kinds of the affinity substances bound thereto can easily respond to variations of a virus that may be created by varying its surface antigen.

Another more specific example of the objective to be trapped is a cell selected from the group consisting of bacterial cell, animal cell, and plant cell. In this case, the affinity support can trap, for example, a receptor constituting a dimer or higher-order multimer such as a vascular endothelial cell growth factor receptor (VEGFR), an epidermal growth factor receptor (EGFR), or a tumor necrosis factor receptor (TNFR).

Another specific example of the objective to be trapped is a non-biological substance, especially an environmentally hazardous substance. Examples of the environmentally hazardous substance include compounds such as dioxin, estrogen, polychlorinated biphenyl, and the like. Other than these compounds, the non-biological substance may be a low molecular weight compound having a molecular weight of 100 to 1,000, preferably 200 to 700.

Another specific example of the objective to be trapped is a multimer or aggregate of drug molecules. The present invention is useful also when association or aggregation of drug molecules becomes a problem during drug preparation. In most cases, drug molecules having the risk of causing such a problem are polypeptide drug molecules. Therefore, examples of such drug molecules include polypeptide drug molecules, and specific examples of the polypeptide drug molecules include insulin, parathyroid hormone and the like.

A sample to be subjected to the affinity support is not particularly limited as long as it contains the above-described objective to be trapped. The sample is usually prepared in a liquid state. The objective to be trapped contained in the sample does not always need to be purified. When the objective to be trapped is purified, the degree of purification is not an issue. According to the present invention, from the viewpoint of microanalysis of the objective to be trapped, there is a case where the degree of treatment such as purification performed on the objective to be trapped contained in the sample is preferably low.

Examples of the sample to be subjected to the affinity support include biological samples prepared from cells, tissues, body fluids, secretions, and excretions of organisms. A typical biological sample prepared from a body fluid is a blood-derived sample. Examples of the blood-derived sample include whole blood, blood plasma, and blood serum. An example of operation that can be performed when a blood-derived sample is prepared from a body fluid is removal of blood cells (more specifically, red blood cells, white blood cells, and/or blood platelets) by centrifugation after addition of an anticoagulant agent (e.g., ethylenediamine tetra-acetic acid, citric acid, or heparin) to blood. Another example of operation that can be performed during preparation of a blood-derived sample is removal of a blood coagulation factor and blood cells after blood coagulation and centrifugation. It is well known that blood undergoes a dynamic change in its components due to the occurrence of disease. Therefore, the blood-derived sample can be used for early diagnosis, follow-up, and/or follow-up after treatment of various diseases by using molecules whose blood levels vary as biomarkers. Further, novel marker molecules in blood have the potential to achieve early diagnosis and high-accuracy diagnosis in the future. Therefore, the blood-derived sample can also be used to search novel marker molecules in blood for the purpose of developing a novel diagnostic method.

By subjecting such a biological sample to the affinity support, it is possible to trap a target substance contained in the sample and examine the trapped target substance.

Another example of the sample to be subjected to the affinity support is an environmental sample prepared from an environmental substance. Examples of the environmental substance include soil, strata, water, air, and the like. An example of operation that can be performed when an environmental sample is prepared from an environmental substance is extraction using an organic solvent (e.g., acetone or toluene).

By subjecting such an environmental sample to the affinity support, it is possible to trap a target substance contained in the sample and examine the trapped target substance.

Another example of the sample to be subjected to the affinity support is an unpurified drug sample. By subjecting such a drug sample to the affinity support, it is possible to remove unnecessary substances (multimers and aggregates of drug molecules) contained in the sample to obtain a purified drug.

The concentration of the objective to be trapped contained in the sample may be, for example, 1 to $10^{12}$ amol/mL, preferably 100 to $10^9$ amol/mL. The sample can be subjected to the affinity support in such a manner that the amount of the objective to be trapped is 0.1 to 500 pmol, preferably 1 to 100 pmol per 1 $cm^2$ of the surface of the support.

3-3. Washing

After the affinity substance bound to the support and the objective to be trapped are bound to each other, the surface of the support may be subjected to a washing process. The washing process can be performed by subjecting the surface of the support to a fluid pressure of 0.01 to 500 MPa, preferably 0.05 to 300 MPa, more preferably 0.1 to 200 MPa to remove unnecessary components. If the fluid pressure is less than the above lower limit, a desired washing effect is less likely to be obtained. If the fluid pressure exceeds the above upper limit, there is a fear that binding between the affinity substance and the trapped objective is cleaved. The affinity support according to the present invention can hold an objective to be trapped by cooperative binding, and therefore can be washed under higher pressure conditions as compared to when a conventional affinity support is used. Such expansion of washing conditions improves the removal efficiency of substances non-specifically adsorbed to the affinity support, which as a result contributes to an improvement in the sensitivity of analysis of the trapped objective.

It is to be noted that a specific washing method is not particularly limited. For example, when having a spherical shape, the affinity support can be washed by vigorously stirring said affinity support in a washing liquid. When having a planar shape, the affinity support can be washed by spraying said affinity support with a high-pressure washing liquid discharged from a spray nozzle. More specifically, in order to subject the specific region on the planar-shaped support to high-pressure washing, a spray nozzle having an inner diameter corresponding to the area of the specific region can be used. This nozzle is constituted from, for example, a double pipe, and an inner pipe can function only as an injection pipe for spraying the surface of the support with a washing liquid, and an outer pipe can function only as a drain pipe for sucking the washing liquid sprayed onto the surface of the support.

3-4. Analysis of Trapped Objective

The trapped objective can be analyzed by an appropriate detection system in a state where said trapped objective remains bound to the affinity support, or said trapped objective is collected by elution from the affinity support (i.e., by releasing the trapped objective by cleaving the binding between the trapped objective and the affinity substance). The elution of the trapped objective from the affinity support can be performed by subjecting the affinity support bound to the trapped objective to an eluate that can be easily selected by those skilled in the art depending on the combination of the trapped objective and the affinity substance.

In the present invention, as an example of the detection system, one based on radioactive assay, enzyme activity assay, fluorescence intensity assay, or emission intensity assay can be used.

For example, when a molecular recognition system to which the affinity support is subjected is an immune system, a detection system based on any solid phase immunoassay may be selected. For example, a detection system based on radioimmunoassay (RIA), enzyme immunoassay (EIA, ELISA), fluorescence immunoassay (FIA), chemiluminescent immunoassay (CLIA), or the like is selected. A label (selected from the group consisting of radioisotope, enzyme, fluorescent substance, and chemiluminescent substance) can be suitably and previously bound to the affinity substance and/or the objective to be trapped by those skilled in the art depending on the kind of detection system used.

When a molecular recognition system to which the affinity support is subjected is an aptamer-receptor protein system, the detection system used can be based on the detecting method used in the above-described immune system. The use of the aptamer-receptor protein system is preferred because the aptamer-receptor protein system is superior to the above-described immune system in specific binding ability and ease of aptamer preparation.

In the present invention, as a preferred example of the detection system other than the above-described detection system, an optical detection system based on surface Plasmon resonance (SFR), sum frequency generation (SFG), local Plasmon resonance (LFR), ellipsometry, or the like is used. Unlike the above-described detection system, such an optical detection system does not require a label.

In the present invention, as another preferred example of the detection system other than the above-described detection system, a detection system based on mass spectrometry is used. In this case, Matrix Assisted Laser Desorption/Ionization (MALDI) mass spectrometry is preferably used as a method of mass spectrometry. For example, a MALDI-TOF (Matrix Assisted Laser Desorption/Ionization-Time of Flight) mass spectrometer, a MALDI-IT (Matrix Assisted Laser Desorption/Ionization-Ion Trap) mass spectrometer, a MALDI-IT-TOF (Matrix Assisted Laser Desorption/Ionization-Ion Trap-Time of Flight) mass spectrometer, a MALDI-FTICR (Matrix Assisted Laser Desorption/Ionization-Fourier Transform Ion Cyclotron Resonance) mass spectrometer, or the like can be used.

A matrix and a matrix solvent can be easily determined by those skilled in the art depending on the kind of objective to be analyzed (i.e., depending on the kind of objective trapped by the affinity support).

As the matrix, for example, α-cyano-4-hydroxycinnamic acid, 2,5-dihydroxybenzoic acid, sinapic acid, 3-aminoquinoline, or the like can be used.

The matrix solvent to be used can be selected from, for example, the group consisting of acetonitrile (ACN), trifluoroacetic acid (TFA), methanol, ethanol, and water. More specifically, an aqueous ACN-TFA solution, an aqueous ACN solution, an aqueous methanol-TFA solution, an aqueous methanol solution, an aqueous ethanol-TFA solution, an ethanol solution, or the like can be used. The concentration of ACN in the aqueous ACN-TFA solution may be, for example, 10 to 90 vol % and the concentration of TFA may be, for example, 0.05 to 1 vol %, preferably 0.05 to 0.1 vol %.

The concentration of the matrix may be, for example, 0.1 to 50 mg/mL, preferably 0.3 to 20 mg/mL, more preferably 0.5 to 20 mg/mL.

When a detection system based on MALDI mass spectrometry is used, a matrix additive (co-matrix) is preferably used in combination with the matrix. The matrix additive can be appropriately selected by those skilled in the art depending on the kind of objective to be analyzed and/or the kind of matrix to be used. For example, as the matrix additive, a phosphonic acid group-containing compound can be used. Specific examples of a compound containing one phosphonic acid group include phosphonic acid, methylphosphonic aid, phenylphosphonic acid, 1-naphthylmethylphosphonic acid, and the like. Specific examples of a compound containing two or more phosphonic acid groups include methylenediphosphonic acid, ethylenediphosphonic acid, ethane-1-hydroxy-1,1-diphosphonic acid, nitrilotriphosphonic acid, ethylenediaminetetraphosphonic acid, and the like. Among the above-mentioned phosphonic acid group-containing compounds, those containing two or more phosphonic acid groups, preferably 2 to 4 phosphonic acid groups in one molecule are preferred.

The use of the phosphonic acid group-containing compound is useful, for example, when an oxyalkylene group-containing group is used as the spacer. The oxyalkylene group-containing group has the property of incorporating positively-charged metal ions around its oxygen atoms, but the metal ions adversely affect the background in mass spectrometry. The use of the phosphonic acid group-containing compound has the effect of reducing such an adverse effect.

It is to be noted that other than the above-mentioned matrix additive, a more common additive selected from, for example, the group consisting of ammonium salt and organic base may be used.

The matrix additive can be prepared as a 0.1 to 10 w/v %, preferably 0.2 to 4 w/v % aqueous solution or matrix solvent solution. A matrix additive solution and a matrix solution can be mixed in a volume ratio of, for example, 1:100 to 100:1, preferably 1:10 to 10:1.

EXAMPLES

Hereinbelow, the present invention will be described more specifically with reference to examples, but is not limited to the following examples. In the following description, the amount of a substance expressed as "%" is based on weight when the substance is solid and on volume when the substance is liquid unless otherwise specified.

Example 1

Trapping of Amyloid β (1-42) by F(Ab')-PEGn Beads Using One Kind of Antibody Fragment (1) Preparation of 6E10 F(ab')-PEGn Beads A procedure for preparing 6E10 F(ab')-PEGn beads is schematically shown in FIG. 1.

Figure 2:
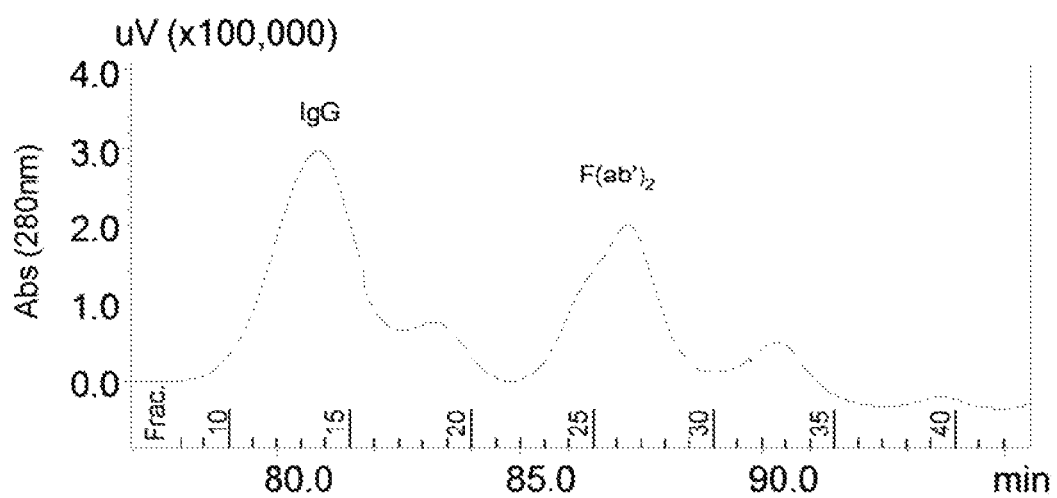
FIG. 2 is a size exclusion chromatogram of a Ficin digest of 6E10.
Figure 3:
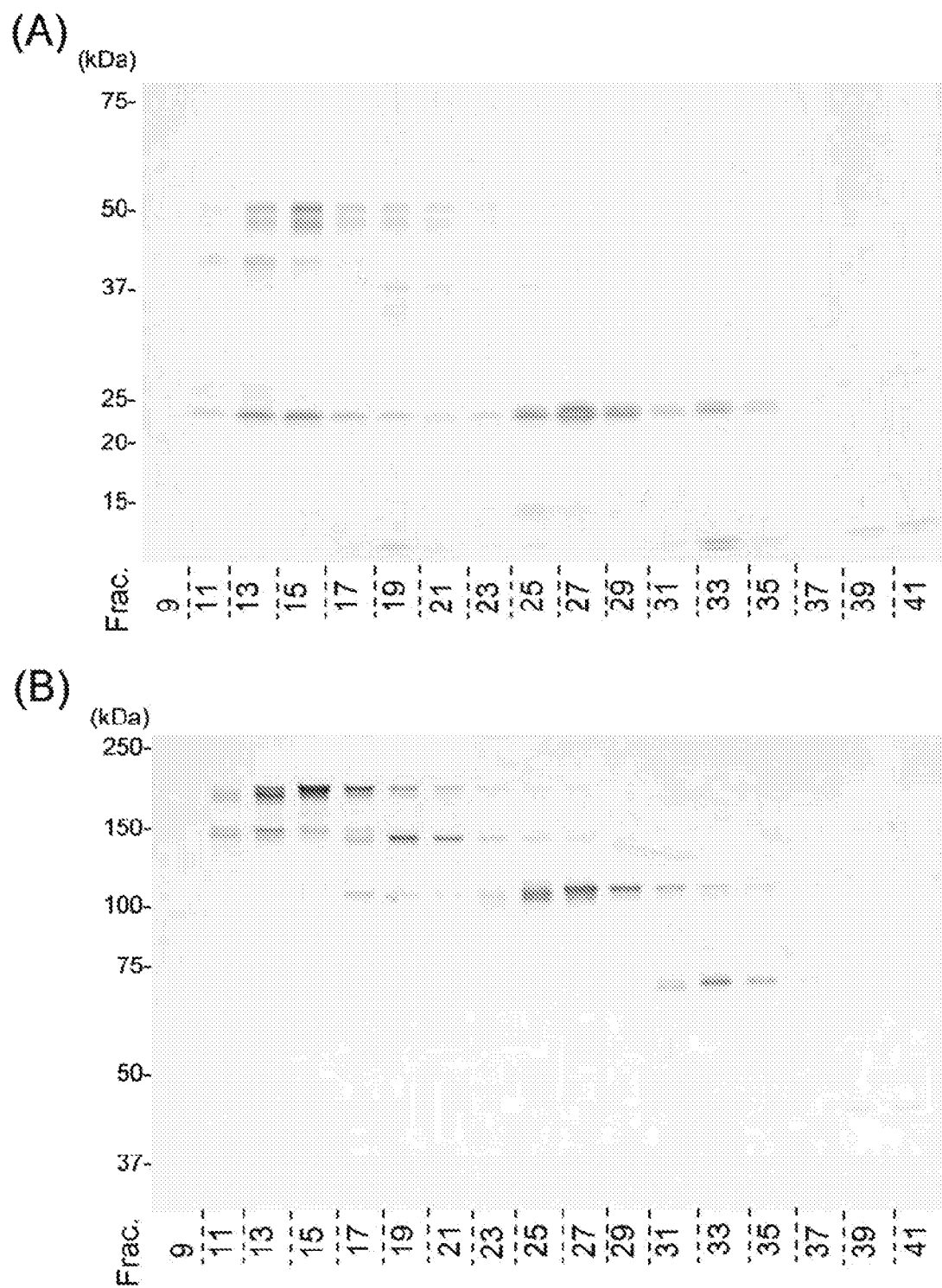
FIG. 3A shows the image of a gel obtained by reducing SDS-PAGE chromatography of the 6E10 digest.
FIG. 3B shows the image of a gel obtained by non-reducing SDS-PAGE chromatography of the 6E10 digest.

First, antibody F(ab') fragments were prepared. More specifically, 250 µg of anti-amyloid β antibody (6E10) whose epitope includes residues 3 to 8 of amyloid β was digested with 1,250 µL of Ficin agarose beads (Thermo) (33% slurry), and a Ficin digest was separated by size exclusion chromatography. FIG. 2 shows the result of separation of the Ficin digest of 6E10 by size exclusion chromatography. FIG. 3A shows the image of a gel obtained by reducing SDS-PAGE chromatography of the fractionated digest of 6E10, and FIG. 3B shows the image of a gel obtained by non-reducing SDS-PAGE chromatography of the fractionated digest of 6E10. In the nature of F(ab')$_2$, a band appears at about 100 kDa under non-reducing conditions, and at 25 kDa under reducing conditions due to the cleavage of the disulfide bonds between the H and L chains. Successful purification of 6E10 F(ab')$_2$ was confirmed by recognizing fractions 24-29 showing a band at 25 kDa under reducing conditions (FIG. 3A) and at about 100 kDa under non-reducing conditions (FIG. 3B). These fractions 24-29 were collected as a F(ab')2 fraction. This 6E10 F(ab')$_2$ fraction was reduced with a 30 mM aqueous 2-mercaptoethylamine (MEA) solution. FIG. 4 shows size exclusion chromatograms of the F(ab')$_2$ fraction before reduction treatment (FIG. 4A) and after reduction treatment (FIG. 4B). It was confirmed from FIG. 4 that 6E10 F(ab') was generated by reduction of the 6E10 F(ab')$_2$ fraction.

Then, 5 μL of amino magnetic beads (Dynabeads M-270 Amine: Invitrogen) (33% slurry) was prepared, and amino groups on the surfaces of the beads were reacted with NHS groups of SM(PEG)n (n=2, 24) at room temperature for 30 minutes to covalently bind PEG to the beads (FIG. 1 shows a case where n=24). Then, F(ab') was reacted with maleimide groups of SM(PEG)n bound to the magnetic beads at room temperature for 30 minutes to covalently bind Flab') to SM(PEG)n.

(2) Preparation of 6E10 IgG-Protein G Beads

For a control experiment, IgG-protein G beads were prepared by affinity binding of 0.75 μg of 6E10 IgG to 5 μL of protein G magnetic beads (Dynabeads Protein G: Invitrogen) (33% slurry).

(3) Amyloid β (1-42) as Antigen

Figure 5:
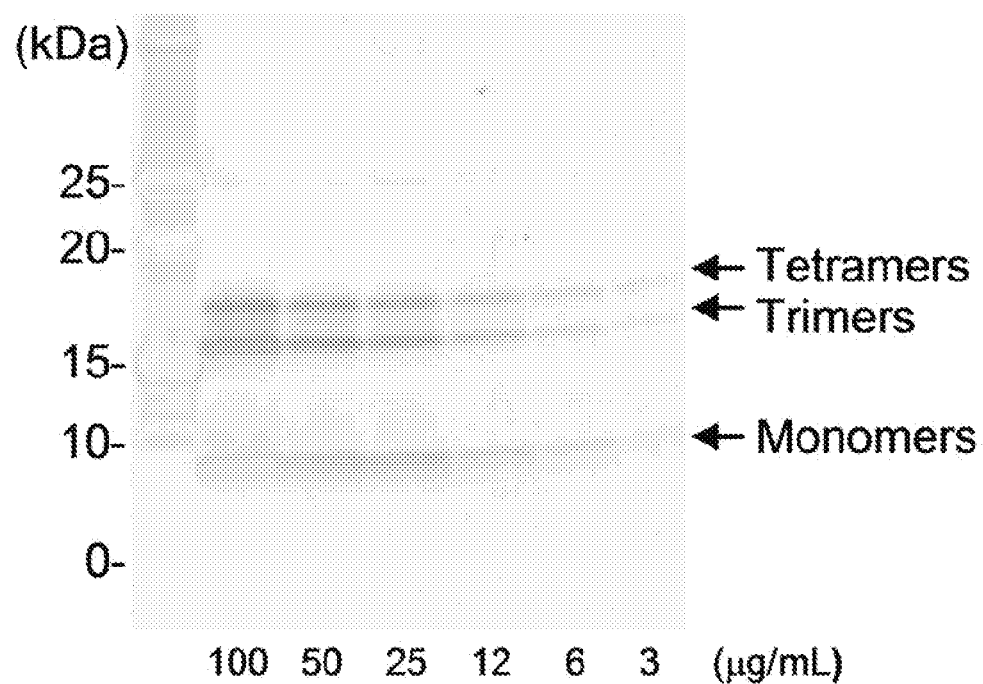
FIG. 5 shows the image of a gel obtained by SDS-PAGE chromatography to determine the presence of aggregates of amyloid β (1-42).

As an antigen, amyloid β (1-42) was used. It is known that C-terminus of amyloid β (1-42) aggregates to form multimers. Therefore, one amyloid β (1-42) aggregate has two or more epitopes for 6E10, and therefore can be used as a material suitable for evaluation of the binding strength of cooperative binding. It is to be noted that the aggregation of amyloid β (1-42) used in this example was confirmed by SDS-PAGE. Amyloid β (1-42) whose concentration was 3 to 100 μg/mL was separated by SDS-PAGE, and the gel was stained with silver. The image of the gel is shown in FIG. 5. As shown in FIG. 5, monomers, trimers, and tetramers of amyloid β (1-42) were detected.

(4) Method for Trapping Amyloid β (1-42) Using Beads

The three kinds of beads, 6E10 F(ab')-PEGn beads (n=2, 24) and 6E10 IgG-protein G beads were washed three times with TBS (10 mM Tris-HCl, 150 mM NaCl, pH 7.4)-1% n-octyl-β-D-thioglycoside (OTG) respectively, and then the beads of each kind were reacted with amyloid β (1-42) at room temperature for 1 hour while they were mixed by inversion. Then, the resultant beads were washed with TBS-1% OTG three times and with H$_2$O once. Then, the beads were subjected to elution with 5 μL of 3 mM HCl twice to obtain an each eluate. In this way, isolation and concentration of an objective to be trapped were performed. The eluate was analyzed by sandwich ELISA and MALDI-TOF MS in the following manner.

(5) Quantitative Determination of Amyloid β (1-42) by Sandwich ELISA

A solution in which anti-amyloid β antibody (4G8) was dissolved at 0.5 μg/mL in a carbonate buffer (15 mM Na$_2$CO$_2$, 35 mM NaHCO$_2$, pH 9.6) was placed in wells of a 96-well plate in an amount of 100 μL/well and allowed to stand at 4° C. overnight. Then, the antibody solution placed in the wells was removed, and a 20% blocking buffer (Nacalai Tesque) was placed in the wells in an amount of 200 μL/well and allowed to stand at room temperature for 2 hours. The wells were washed with 300 μL/well of a washing buffer (10 mM Na$_2$HPO$_4$, 1.76 mM KH$_2$PO$_4$, 137 mM NaCl, 2.7 mM KCl, 0.1% Tween) three times.

A solution in which amyloid β (1-42) was dissolved at a known concentration in a reaction buffer (10 mM Na$_2$HPO$_4$, 1.76 mM KH$_2$PO$_4$, 137 mM NaCl, 2.7 mM KCl, 0.1% Tween, 5% blocking buffer (Nacalai Tesque)), and a sample obtained by diluting the eluate obtained in the above (4) with the above-described reaction buffer 100-fold were placed in the wells separately in an amount of 100 μL/well and shaken at room temperature for 1 hour. The wells were washed with 300 μL/well of the washing buffer five times, and then a 0.1 μg/mL HPR-labeled anti-amyloid β antibody (6E10-HPR) was placed in the wells in an amount of 100 μL/well and shaken at room temperature for 1 hour. The wells were washed with 300 μL/well of a washing buffer (PBS-0.1% Tween) five times, and then TMB was placed in the wells in an amount of 100 μL/well and shaken at room temperature for 15 minutes. After 1N H$_2$SO$_4$ was added to the wells in an amount of 100 μL/well, absorbance (450 nm/650 nm) of the wells was measured using a plate reader.

(6) MALDI-TOF MS

On a MALDI plate, 1 μL of the eluate obtained in the above (4) and 1 μL of a solution of α-cyano-4-hydroxycinnamic acid (CHCA) in which CHCA was dissolved at 0.5 mg/mL in a 50% aqueous acetonitrile solution containing 0.1% trifluoroacetic acid were dropped and mixed to obtain a sample. The sample was analyzed using AXIMA performance (Shimadzu Corporation) in linear mode. In order to allow a comparison to be made among samples, all the samples were analyzed in raster mode under fixed conditions where the number of profiles was 500, the number of shots per profile was 5, and the number of laser shots was 100 points. A criterion for peak detection was S/N≥3.

(7) Evaluation of Amount of Amyloid β (1-42) Trapped by 6E10 F(ab')-PEGn Beads

Figure 6:
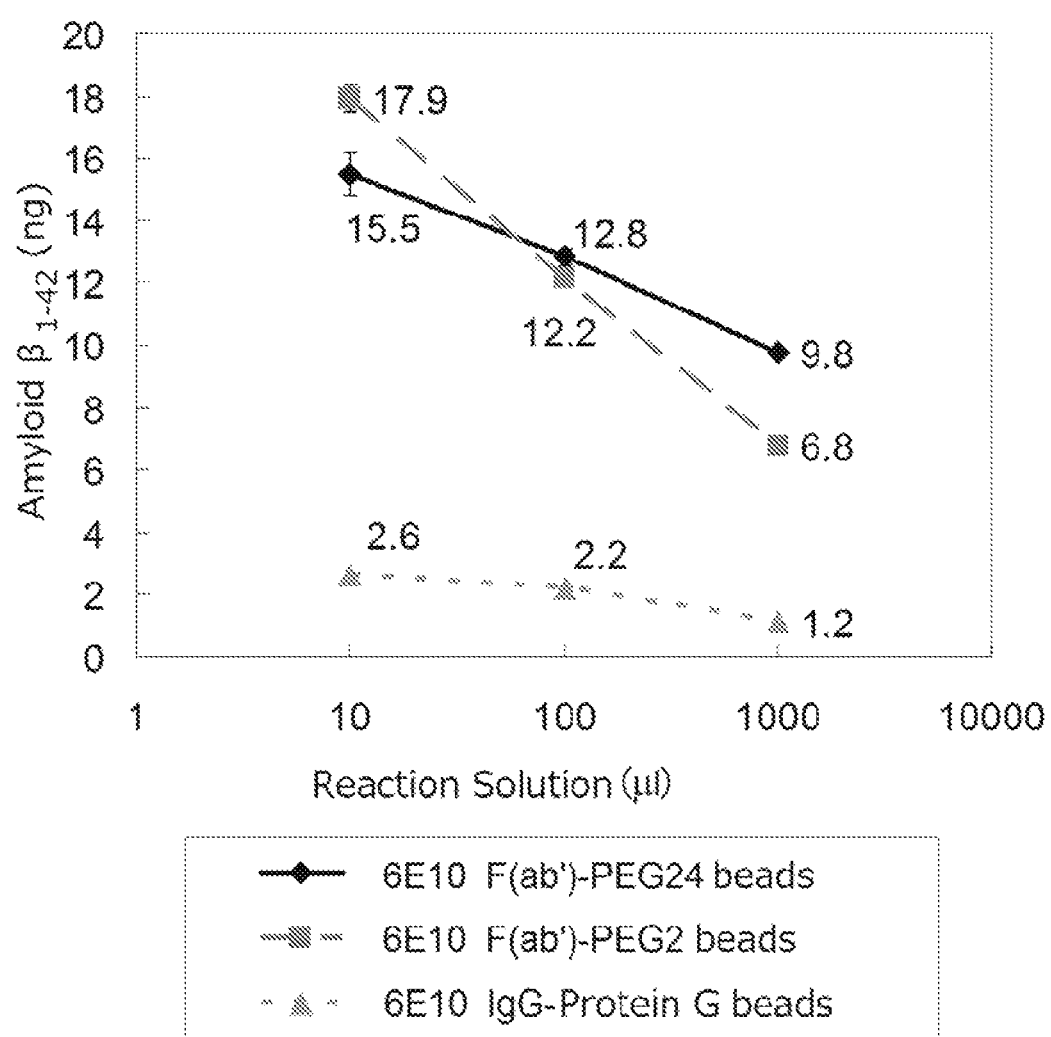
FIG. 6 is a graph showing the amounts of trapped amyloid β (1-42) when reaction solutions containing a fixed amount (100 ng) of amyloid β (1-42) and having different liquid amounts (10, 100, and 1,000 μL) were subjected to various affinity supports (6E10 F(ab')-PEG$_{24}$ beads, 6E10 F(ab')-PEG$_2$ beads, and 6E10 IgG-protein G beads), respectively.

Isolation and concentration of amyloid β (1-42) were performed using the different kinds of beads (i.e, 6E10 F(ab')-PEG$_{24}$ beads, 6E10 F(ab')-PEG$_2$ beads, and 6E10 IgG-protein G beads) under conditions where the amount of amyloid β (1-42) as an antigen was set to a fixed value of 100 ng, the number of the beads of each kind was set to a fixed value of 10$^7$, and the liquid amounts of a reaction solution were set to 10, 100, and 1,000 μL (i.e., variations of concentration levels of antibody and antigen were 1×, 10×, and 100×). The amount of the antigen trapped for isolation and concentration was measured by ELISA. A graph representing the amount of trapped amyloid β (1-42) is shown in FIG. 6. The amount of the antigen trapped by the 6E10 F(ab')-PEG$_{24}$ beads was 5.9 to 8.5 times larger than that trapped by the 6E10 IgG-protein G beads, and the amount of the antigen trapped by the 6E10 F(ab')-PEG$_2$ beads was 5.6 to 6.9 times larger than that trapped by the 6E10 IgG-protein G beads.

All the three kinds of beads showed a tendency that the amount of the trapped antigen was reduced as the amount of the reaction solution was increased. However, the rate of the reduction was lower when the 6E10 F(ab')-PEG$_{24}$ beads were used than when the 6E10 F(ab')-PEG$_2$ beads were used. When the amount of the reaction solution was 1,000 μL, the amount of the trapped antigen was largest when the 6E10 F(ab')-PEG$_{24}$ beads were used. Here, the rate of binding of the antigen to the antibody varies depending on the respective molar concentrations of the antibody, and the antigen and the association rate constant (ka) and dissociation rate constant (kd) of the antibody. According to the result of SPR described in the Non-Patent Document 2 (Proceedings of the Japan Academy, Ser. B, Physical and Biological Sciences 2011; 87(9): 603-16), there is no difference in the association rate constant (ka) of an antigen-antibody reaction between when cooperative binding occurs and when cooperative binding does not occur, but the dissociation rate constant (kd) of the antigen-antibody reaction is lower when cooperative binding occurs than when cooperative binding does not occur.

From the result that the amount of the trapped antigen was larger when the F(ab')-PEG$_{24}$ beads were used than when the F(ab')-PEG$_2$ beads were used, it is considered that preferred cooperative binding (i.e., binding with a lower kd) occurred when the F(ab')-PEG$_{24}$ beads bind to the antigen. This indicates that the F(ab')-PEG$_{24}$ beads can be used as a more effective tool for trapping molecules whose concentration in a biological sample is lower.

(8) Evaluation of Detection Limit by Mass Spectrometer

Figure 7:
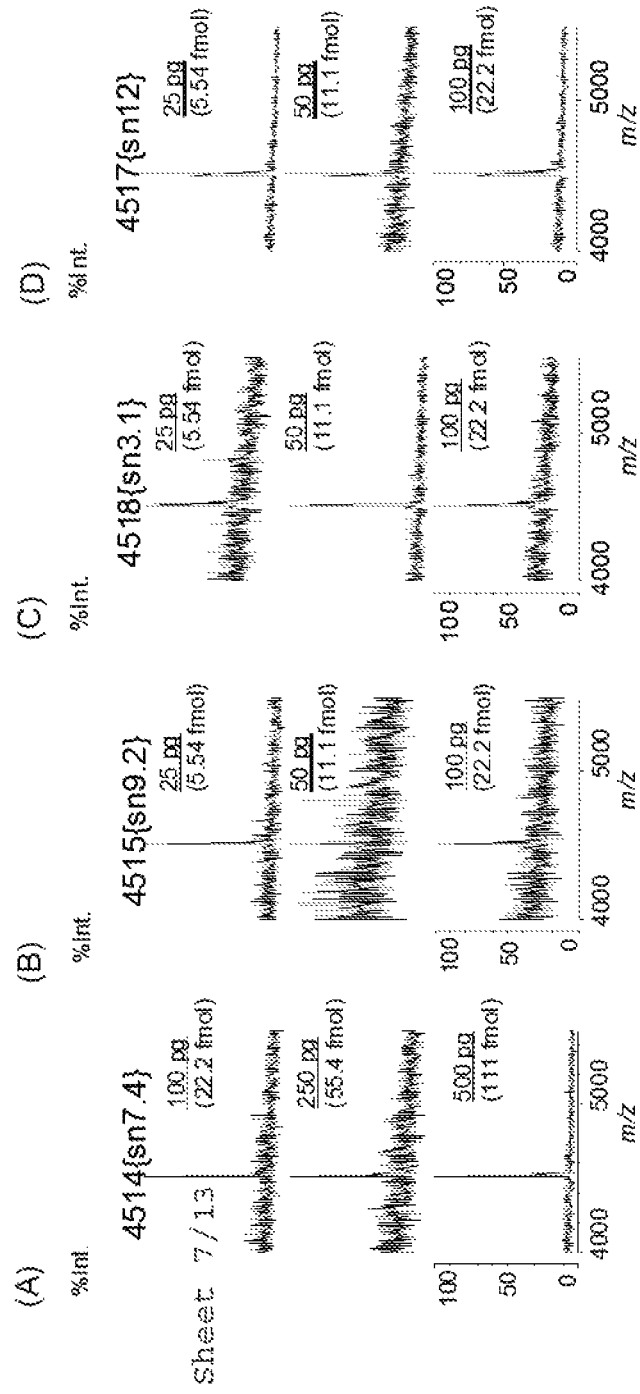
FIG. 7 shows a comparison of MALDI-TOF MS spectra obtained when different amounts of amyloid β (1-42) were trapped using various affinity supports (6E10 IgG-protein G beads (FIG. 7A), 6E10 F(ab')-PEG$_2$ beads (FIG. 7B), and 6E10 F(ab')-PEG$_{24}$ beads (FIG. 7C) and the MALDI-TOF MS spectrum of pure amyloid β (1-42) (FIG. 7D).

An experiment was performed to verify that the amount of antigen required for detection by a mass spectrometer is smaller when the method according to the present invention is used than when a conventional immunoprecipitation method is used (i.e., than when the 6E10 IgG-protein G beads are used). FIG. 7 shows the MALDI-TOF MS spectra of amyloid β (1-42) eluates obtained when the 6E10 IgG-protein G beads were used (FIG. 7A), the MALDI-TOF MS spectra of amyloid β (1-42) eluates obtained when the 6E10 F(ab')-PEG$_2$ beads were used (FIG. 7B), the MALDI-TOF MS spectra of amyloid β (1-42) eluates obtained when the 6E10 F(ab')-PEG$_{24}$ beads were used (FIG. 7C), and the MALDI-TOF MS spectra of pure amyloid β (1-42) (directly) spotted onto a MALDI plate without being trapped by beads (FIG. 7D). The detection limits of amyloid β (1-42) in all the cases are shown in Table 1.

TABLE 1

Detection Limit (S/N ≥ 3)

| 6E10 IgG-protein G | 6E10 F(ab')-PEG$_2$ | 6E10 F(ab')-PEG$_{24}$ | Directly Spotting |
|---|---|---|---|
| 100 pg (22.2 fmol) | 25 pg (5.54 fmol) | 25 pg (5.54 fmol) | 25 pg (5.54 fmol) |

When a conventional immunoprecipitation method was used, that is, when the 6E10 IgG-protein G beads were used, the amount of amyloid β (1-42) required for detection by MALDI-TOF MS was 100 pg. On the other hand, when the method according to the present invention was used, that is, when the 6E10 F(ab')-PEG$_{24}$ beads or the 6E10 F(ab')-PEG$_2$ beads were used, the amount of amyloid β (1-42) required for detection by MALDI-TOF MS was only 25 pg. This indicates that the amount of antigen required for detection by a mass spectrometer is smaller when the method according to the present invention is used than when the conventional immunoprecipitation method is used. In addition, the detection level achieved by the method according to the present invention was equivalent to the detection limit achieved by directly spotting amyloid β (1-42) onto a MALDI plate. That is, the method according to the present invention makes it possible to collect amyloid β (1-42) from a sample at a rate nearly 100%.

Example 2

Trapping of Amyloid β (1-28) by 6E10/4G8 F(ab')-PEGn Beads Using Two Kinds of Antibody Fragments When molecules forming homomultimers such as amyloid β (1-42) are an objective to be trapped, the amount of the trapped objective can be increased when the 6E10 F(ab')-PEGn beads of Example 1 derived from one kind of antibody are used as compared to when the 6E10 IgG-protein G beads are used.

On the other hand, in this example, beads having two kinds of F(ab') fragments were prepared based on the premise that, when a single molecule of an antigen is an objective to be trapped, at least two kinds of antibody-derived F(ab') fragments that recognize two or more sites in the antigen single molecule are necessary to increase the amount of the trapped antigen.

(1) Preparation of Various F(ab')-PEG$_{24}$ Beads
(1-1) Preparation of 6E10/4G8 F(ab')-PEG$_{24}$ Beads One of two kinds of F(ab') fragments was prepared in the same manner as in Example 1 from anti-amyloid β antibody 6E10 whose epitope includes 3-8 residues of amyloid β, and the other was prepared from anti-amyloid β antibody 4G8 whose epitope includes 18-22 residues of amyloid β. The 4G8 antibody is an IgG2b, and therefore F(ab')$_2$ cannot be obtained by Ficin or Pepsin. For this reason, F(ab')$_2$ was obtained by lysyl-end peptidase (LysC). More specifically, 100 μg of 4G8 was digested with 500 ng of LysC for 2.5 hours, and then a LysC digest was separated by size exclusion chromatography.

Figure 8:
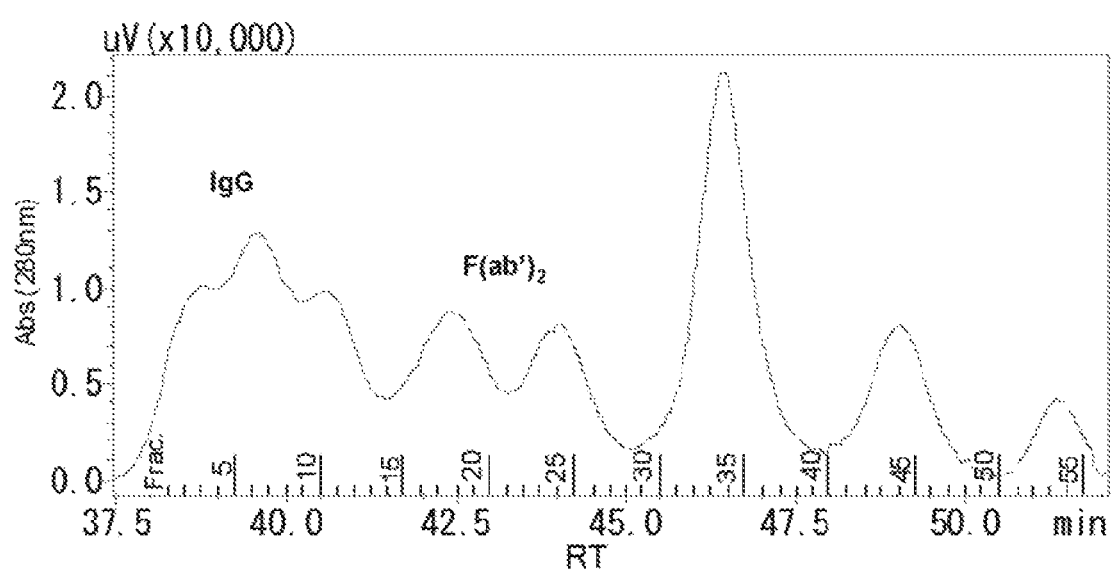
FIG. 8 is a size exclusion chromatogram of a LysC digest of 4G8.
Figure 9:
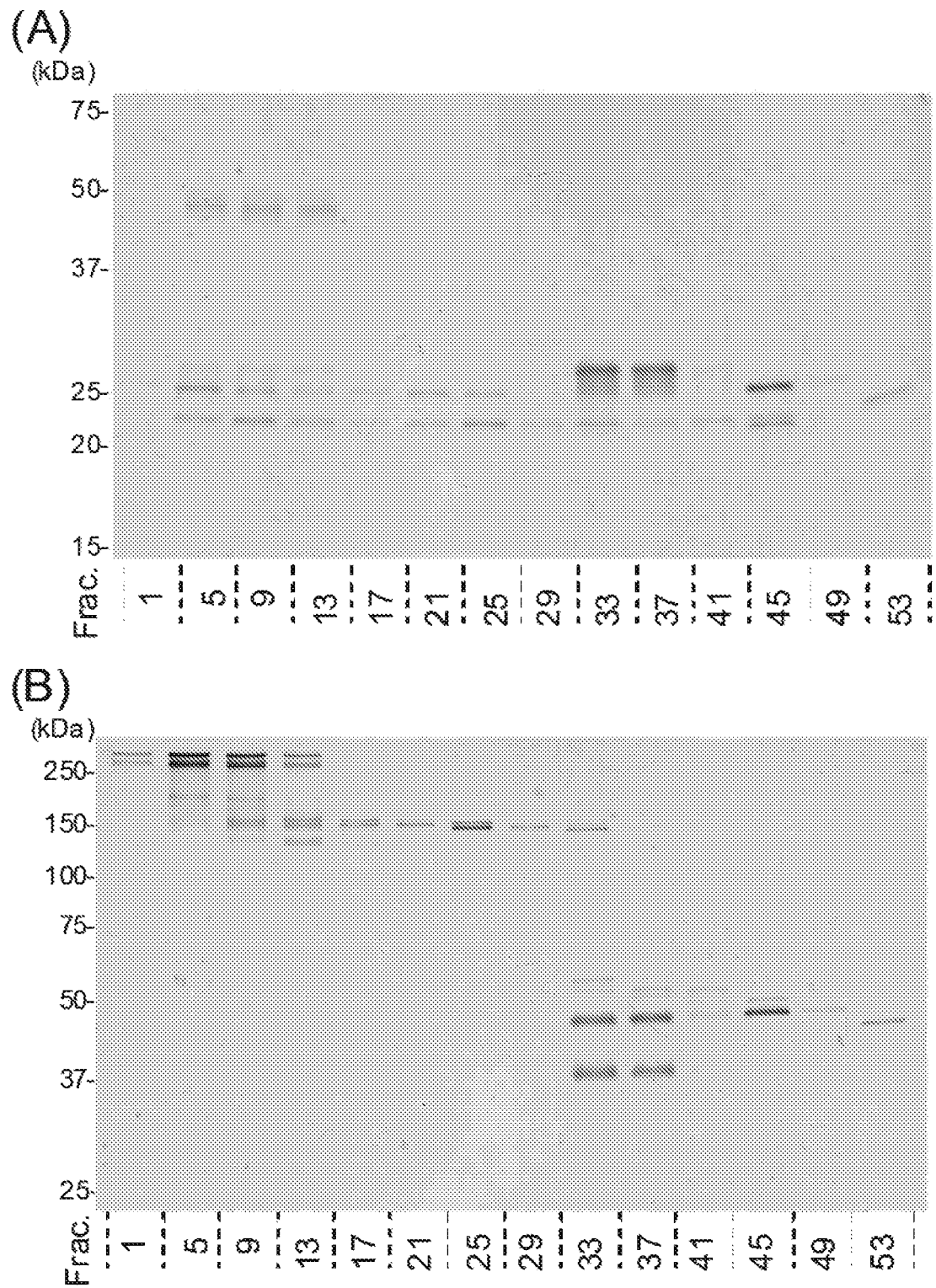
FIG. 9A shows the image of a gel obtained by reducing SDS-PAGE chromatography of the 4G8 digest.
FIG. 9B shows the image of a gel obtained by non-reducing SDS-PAGE chromatography of the 4G8 digest.

FIG. 8 shows the result of separation of the LysC digest of 4G8 by size exclusion chromatography. Further, FIG. 9 shows the image of a gel obtained by reducing SDS-PAGE chromatography of the fractionated digest of 4G8 (FIG. 9A) and the image of a gel obtained by non-reducing SDS-PAGE chromatography of the fractionated digest of 4G8 (FIG. 9B). The fractions 16-29 showing a band at about 150 kDa under non-reducing conditions and at 25 kDa under reducing conditions were collected as a 4G8 F(ab')$_2$ fraction. The 4G8 F(ab')$_2$ fraction was reduced to obtain 4G8 F(ab').

Beads to each of which two kinds of F(ab') fragments were bound via PEG, that is, 6E10/4G8 F(ab')-PEG$_{24}$ beads were prepared in the same manner as in (1) in Example 1 except that the 4G8 F(ab') fraction and the 6E10 F(ab') fraction obtained in (1) in Example 1 were used in 1:1 (molar ratio) as the F(ab') fraction.

(1-2) Preparation of 6E10 F(ab')-PEG$_{24}$ Beads and 4G8 F(Ab')-PEG$_{24}$ Beads For reference experiments, the same 6E10 F(ab')-PEG$_{24}$ beads as used in Example 1 were prepared, and 4G8 F(ab')-PEG$_{24}$ beads were prepared in the same manner as in (1) in Example 1 except that the 4G8 F(ab') fraction was used as the F(ab') fraction.

(2) Preparation of Various IgG-Protein G Beads
(2-1) Preparation of 6E10/4G8 IgG-Protein G Beads Protein G beads to each of which two kinds of antibodies were bound, that is, 6E10/4G8 IgG-protein G beads were prepared in the same manner as in (2) in Example 1 except that the 4G8 IgG and the 6E10 IgG were used in 1:1 (molar ratio).

(2-2) Preparation of 6E10 IgG-Protein G Beads and 4G8 IgG-Protein G Beads

For control experiments, the same 6E10 IgG-protein G beads as used in Example 1 were prepared, and 4G8 IgG-protein G beads were prepared in the same manner as in (2) in Example 1 except that 4G8 IgG was used as the antibody.

(3) Amyloid β (1-28) as Antigen

As an antigen, amyloid β (1-28) was used. Amyloid β (1-28) is present as a single molecule and an aggregate in a solution.

Figure 10:
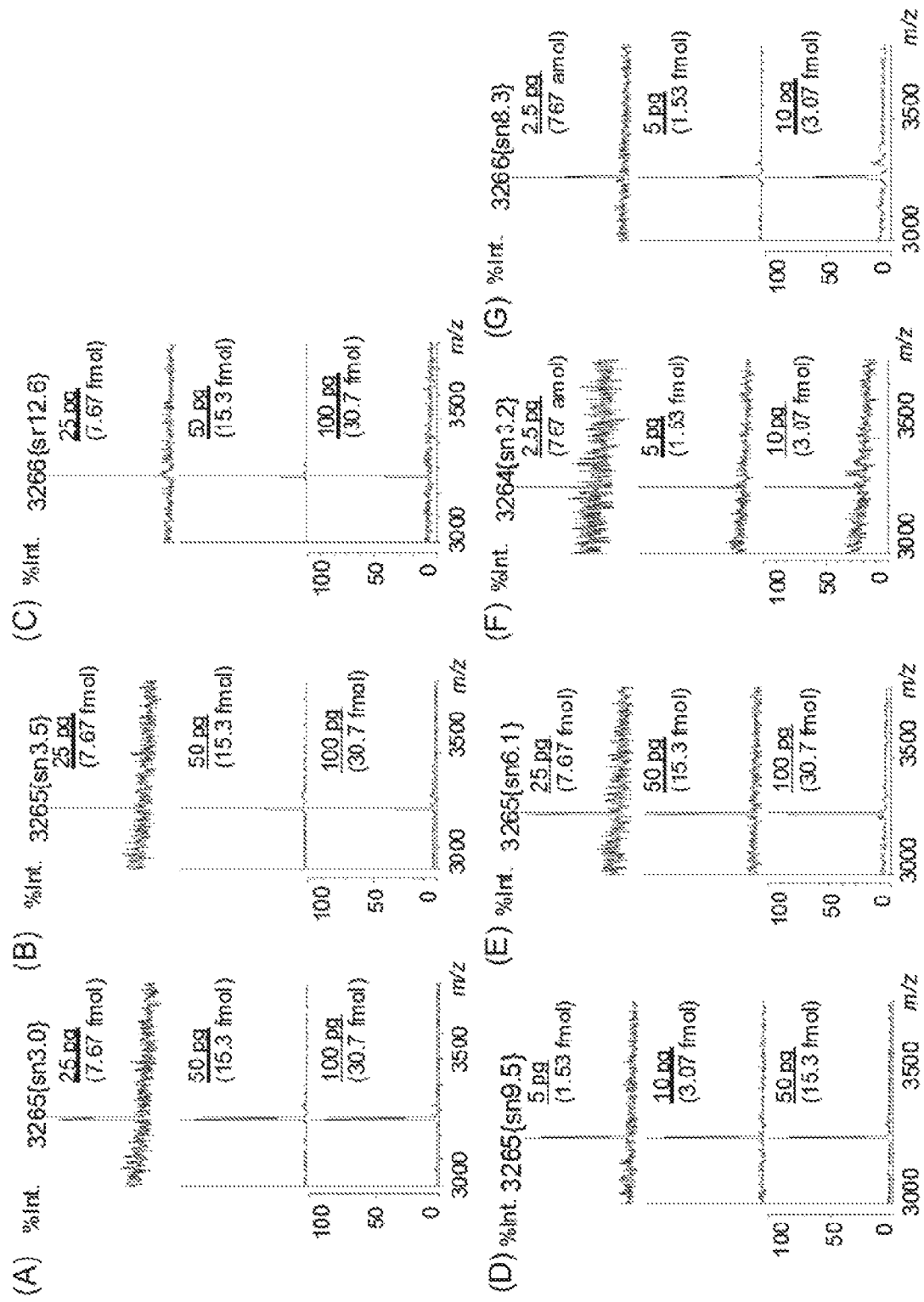
FIG. 10 shows a comparison of MALDI-TOF MS spectra obtained when different amounts of amyloid β (1-28) were trapped using various affinity supports (6E10 IgG-protein G beads (FIG. 10A), 4G8 IgG-protein G beads (FIG. 10B), 6E10/4G8 IgG-protein G beads (FIG. 10C), 6E10 F(ab')-PEG$_{24}$ beads (FIG. 10D), 4G8 F(ab')-PEG$_{24}$ beads (FIG. 10E), and 6E10/4G8 F(ab')-PEG, beads (FIG. 10F) and the MALDI-TOF MS spectrum of pure amyloid β (1-28) (FIG. 10G).

(4) Evaluation of Amount of Amyloid β (1-28) Trapped by 6E10/4G8 F(ab')-PEG" Beads Amyloid β (1-28) was trapped in the same manner as in (4) in Example 1 using the above-described affinity beads (6E10/4G8 F(ab')-PEG$_{24}$ beads, 6E10 F(ab')-PEG$_{24}$ beads, 4G8 F(ab')-PEG$_{24}$ beads, 6E10/4G8 IgG-protein G beads, 6E10 IgG-protein G beads, and 4G8 IgG-protein G beads). Further, MALDI-TOF MS was performed using a mass spectrometer in the same manner as in (6) in Example 1 to determine detection limits. FIG. 10 shows the MALDI-TOF MS spectra of amyloid β (1-28) eluates obtained when the 6E10 IgG-protein G beads were used (FIG. 10A), the MALDI-TOF MS spectra of amyloid β (1-28) eluates obtained when the 4G8 IgG-protein G beads were used (FIG. 10B), the MALDI-TOF MS spectra of amyloid (1-28) eluates obtained when the 6E10/4G8 IgG-protein G beads were used (FIG. 10C), the MALDI-TOF MS spectra of amyloid β (1-28) eluates obtained when the 6E10 F(ab')-PEG2, beads were used (FIG. 10D), the MALDI-TOF MS spectra of amyloid β (1-28) eluates obtained when the 4G8 F(ab')-$PEG_{24}$ beads were used (FIG. 10E), the MALDI-TOF MS 10 spectra of amyloid β (1-28) eluates obtained when the 6E10/4G8 F(ab')-$PEG_{24}$ beads were used (FIG. 10F), and the MALDI-TOF MS spectra of pure amyloid β (1-28) (directly) spotted onto a MALDI plate without being trapped by beads (FIG. 10G). The detection limits (S/N≥3) of amyloid β (1-28) in all the cases are shown in Table 2.

TABLE 2

| | Detection Limit (S/N ≥ 3) | | |
|---|---|---|---|
| | IgG- protein G | F(ab')-$PEG_{24}$ | Directly Spotting |
| 6E10 | 25 pg (7.67 fmol) | 5 pg (1.53 fmol) | 2.5 pg (767 amol) |
| 4G8 | 25 pg (7.67 fmol) | 25 pg (7.67 fmol) | |
| 6E10/4G8 | 25 pg (7.67 fmol) | 2.5 pg (767 amol) | |

When the three kinds of IgG-protein G beads (6E10/4G8 IgG-protein beads, 6E10 IgG-protein G beads, and 4G8 IgG-protein G beads) were used, the detection limit was 25 pg in all the cases. On the other hand, when the 6E10 F(ab')-$PEG_{24}$ beads were used, the detection limit was 5 pg. That is, sensitivity when the 6E10 F(ab')-$PEG_N$ beads were used was 5 times higher than that when the IgG-protein G beads of each kind were used. It is considered that this is because space is created between each of the beads and -F(ab') by PEG insertion so that steric hindrance becomes less likely to occur and the binding strength of antigen-antibody reaction is enhanced.

On the other hand, the detection limit when the 4G8 F(ab')-$PEG_{24}$ beads were used was 25 pg that was the same as that when the 4G8 IgG-protein G beads were used. There is a case where F(ab') fragmentation of IgG reduces the binding strength between antigen and antibody, but it has been found that the effect of PEG insertion to enhance the binding strength between antigen and antibody can compensate for a reduction in the binding strength between antigen and antibody due to the fragmentation of IgG.

When the 6E10/4G8 F(ab')-$PEG_{24}$ beads were used, the detection limit was 2.5 pg, which was equivalent level to the detection limit achieved by directly spotting amyloid β (1-28) onto a MALDI plate.

Here, from a simple calculation of the binding strengths of 6E10 F(ab') and 4G8 F(ab'), the detection limit when the 6E10/4G8 F(ab')-$PEG_{24}$ beads are used is estimated to be about 15 pg that is the average of the detection limit when the 6E10 F(ab')-$PEG_{24}$ beads were used (5 pg) and the detection limit when the 4G8 F(ab')-$PEG_{24}$ beads were used (25 pg). However, the detection limit when the 6E10/4G8 F(ab')-$PEG_{24}$ beads were used was 2.5 pg that was ⅙ of the estimated detection limit. It is considered that this is because that binding strength is enhanced by cooperative binding achieved by the two kinds of antibody fragments (6E10 F(ab') and 4G8 F(ab')), which recognize different epitopes to each other, on each of the beads. On the other hand, the S/N ratio when the 6E10/4G8 F(ab')-$PEG_{24}$ beads were used was lower than that when pure amyloid β (1-28) was analyzed, from which it is considered that the eluate contained minute quantities of impurities (low-molecular compounds, metal ions, etc.).

Example 3

Trapping of Amyloid β (1-28) Spiked in Human Plasma

In order to measure target biomolecules in a biological sample by a mass spectrometer, it is important to eliminate impurities by isolating and concentrating the target molecules. In this example, an experiment was performed to examine the ability of the F(ab')-PEGn beads to eliminate impurities by isolating and concentrating an objective to be trapped. As a biological sample, human plasma was used.

One milliliter of a sample was prepared by spiking 1 ng (307 fmol) of amyloid β (1-28) in plasma obtained by diluting 50 μL of human plasma 20-fold with TBS-1% OTG. Amyloid β (1-28) in the sample was isolated and concentrated in the same manner as in (4) in Example 1. However, in this example, washing with TBS-1% OTG performed in Example 1 three times after the reaction between the beads and the sample was performed 5 times to eliminate impurities non-specifically adsorbed to the beads.

Figure 11:
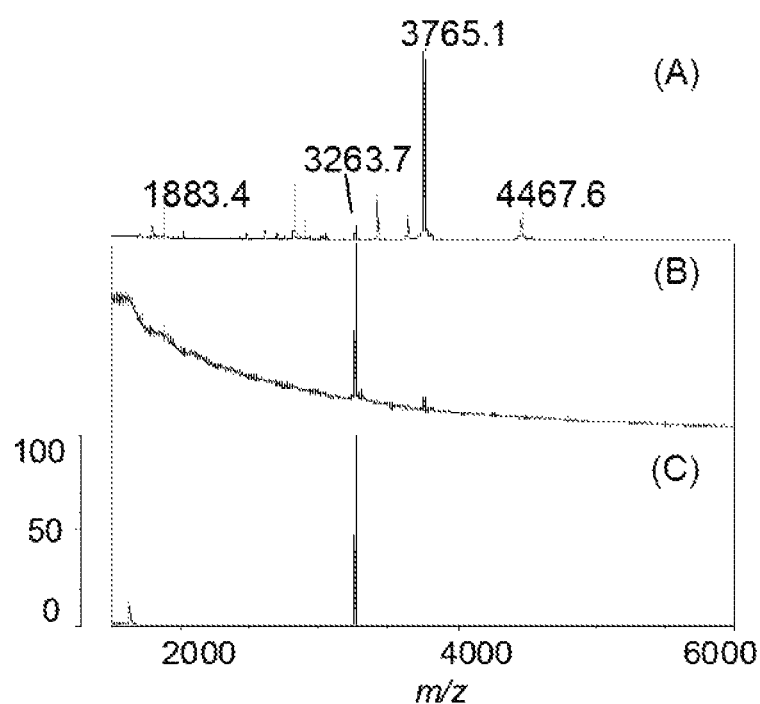
FIG. 11 shows mass spectra obtained when human plasma in which amyloid β (1-28) was spiked was subjected to an affinity support (6E10 F(ab')-PEG$_{24}$ beads).

For a reference experiment, amyloid β (1-28) was isolated and concentrated using the 6E10 F(ab')-$PEG_{24}$ beads, and was than analyzed by a mass spectrometer in the same manner as in (6) in Example 1. The thus obtained mass spectrum is shown in FIG. 11(A). As shown in FIG. 11(A), many peaks other than the peak of amyloid β (1-28) were detected.

It is known that human anti-mouse antibody (HAMA) is present in human blood. Since 6E10 and 4G8 are mouse-derived IgGs, molecules of such an antibody bind thereto. In order to prevent such binding, before the plasma sample in which amyloid β (1-28) was spiked and the beads were mixed, human anti-mouse antibody contained in the plasma was removed by mixing the plasma sample and 50 uL of protein G agarose and incubating the mixture at 4° C. for 30 minutes. Then, mass spectrometry was performed in the same manner. The thus obtained mass spectrum is shown in FIG. 11(B). As shown in FIG. 11(B), the many peaks other than the peak of amyloid β (1-28) were removed by removing human anti-mouse antibody. On the other hand, a high background spectrum was observed.

PEG has the property of incorporating positively-charged metal ions around negatively-charged oxygen atoms thereof. When being incorporated into PEG and then released from PEG by elution with HCl, metal ions contained in the reaction buffer and the plasma have an influence on analysis performed by the mass spectrometer. It is considered that this influence causes a high background in the mass spectrum. For this reason, 1 μL of a 2% aqueous methanediphosphonic acid (MDPNA) solution having the effect of reducing the background due to metal ions was mixed as a comatrix on the MALDI plate, and then mass spectrometry was performed. The thus obtained mass spectrum is shown in FIG. 11(C). As shown in FIG. 11(C), a spectrum having a high S/N ratio was obtained. It is to be noted that the concentration of CHCA at which the best signal was obtained when 2% MDPNA was used in combination therewith was 5 mg/mL.

Under the above conditions, amyloid (1-28) spiked in plasma was isolated and concentrated using the F(ab')-

Figure 12:
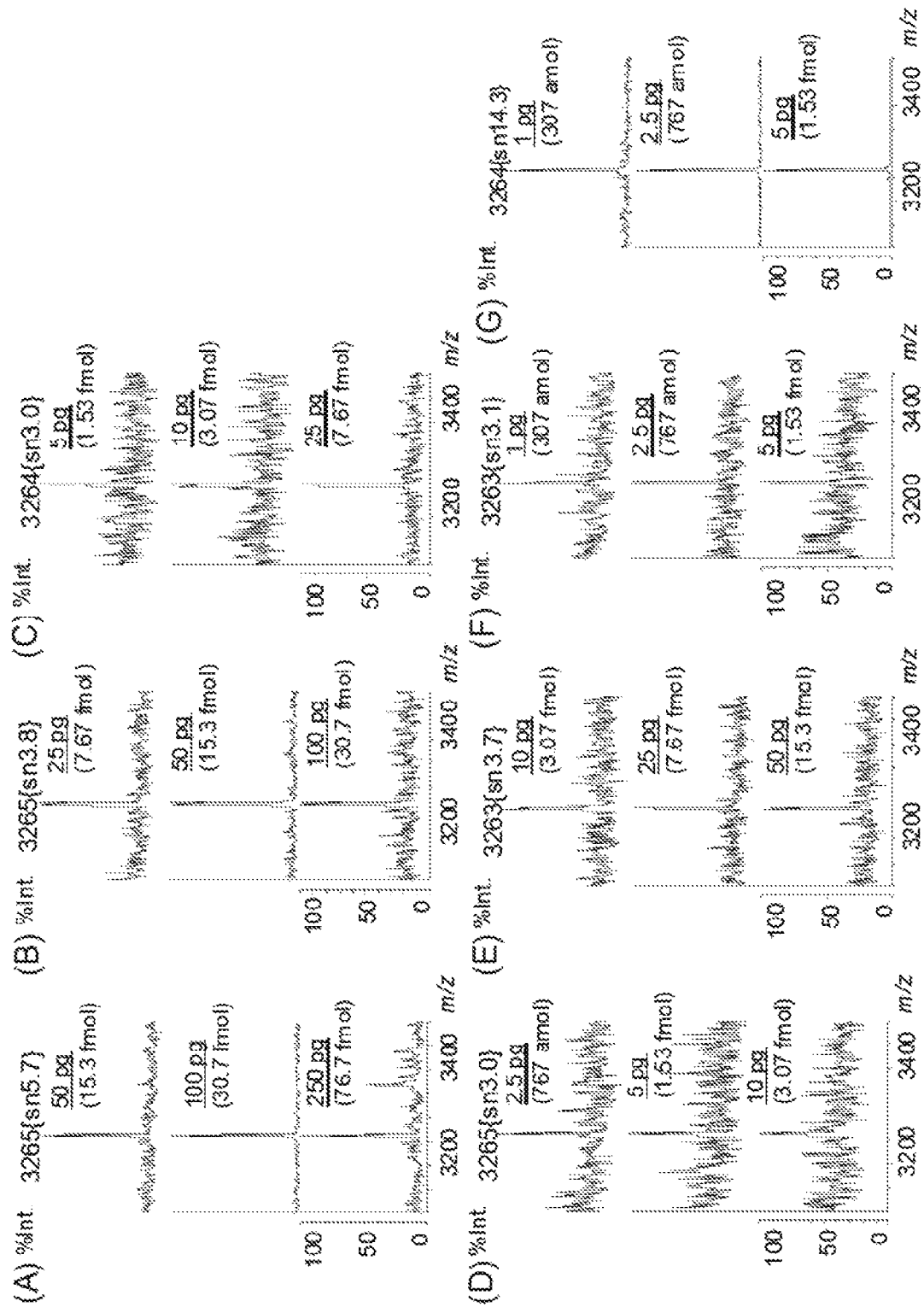
FIG. 12 shows a comparison of MALDI-TOF MS spectra obtained when different amounts of amyloid β (1-28) spiked in human plasma were trapped using various affinity supports (6E10 IgG-protein G beads (FIG. 12A), 4G8 IgG-protein G beads (FIG. 12B), 6E10/4G8 IgG-protein G beads (FIG. 12C), 6E10 F(ab')-PEG$_{24}$ beads (FIG. 12D), 4G8 F(ab')-PEG$_{24}$ beads (FIG. 12E), and 6E10/4G8 F(ab')-PEG$_{24}$ beads (FIG. 12F) and the MALDI-TOF MS spectrum of pure amyloid β (1-28) (FIG. 12G).

PEG$_{24}$ beads and analyzed by the mass spectrometer to determine the detection limit of amyloid β (1-28). FIG. 12 shows the MALDI-TOF MS spectra of amyloid β (1-28) eluates obtained when the 6E10 IgG-protein C beads were used (FIG. 12A), the MALDI-TOF MS spectra of amyloid β (1-28) eluates obtained when the 4G8 IgG-protein G beads were used (FIG. 12B), the MALDI-TOF MS spectra of amyloid β (1-28) eluates obtained when the 6E10/4G8 IgG-protein G beads were used (FIG. 12C), the MALDI-TOF MS spectra of amyloid β (1-28) eluates obtained when the 6E10 F(ab')-PEG$_{24}$ beads were used (FIG. 12D), the MALDI-TOF MS spectra of amyloid β (1-28) eluates obtained when the 4G8 F(ab')-PEG$_{24}$ beads were used (FIG. 12E), the MALDI-TOF MS spectra of amyloid β (1-28) eluates obtained when the 6E10/4G8 F(ab')-PEG$_{24}$ beads were used (FIG. 12F), and the MALDI-TOF MS spectra of pure amyloid β (1-28) (directly) spotted on a MALDI plate without being trapped by beads (FIG. 12G). The detection limits (S/N≥3) of amyloid β (1-28) in all the cases are shown in Table 3.

TABLE 3

| | Detection Limit (S/N ≥ 3) | | |
|---|---|---|---|
| | IgG-proteinG | F(ab')-PEG$_{24}$ | Directly Spotting |
| 6E10 | 50 pg (15.3 fmol) | 2.5 pg (767 amol) | 1 pg (307 amol) |
| 4G8 | 25 pg (7.67 fmol) | 10 pg (3.07 fmol) | |
| 6E10/4G8 | 5 Pg (1.53 fmol) | 1 pg (307 amol) | |

The detection limit when pure amyloid β (1-28) was detected by the mass spectrometer without being trapped by beads was 1 pg (307 amol) (FIG. 12G). The evaluation point of this example is to achieve a mass spectrometric detection level close to 1 pg (307 amol) by isolating and concentrating amyloid β (1-28) in plasma using the F(ab')-PEG$_{24}$ beads. It is to be noted that a detection limit of 1 pg (307 amol) achieved in this example is lower than that achieved in Example 2 using only the matrix CHCA. This is because the combined use of the matrix and the comatrix MDPNA reduces the background, which increases the S/N ratio.

Amyloid β (1-28) spiked in plasma was isolated and concentrated using the three kinds of F(ab')-PEG$_{24}$ beads (6E10 F(ab')-PEG$_{24}$ beads, 4G8 F(ab')-PEG$_{24}$ beads, and 6E10/4G8 F(ab')-PEG$_{24}$ beads) and the three kinds of IgG-protein G beads (6E10-protein G beads, 4G8-protein G beads, and 6E10/4G8-protein G beads). As a result, the lowest level of amyloid β (1-28) (1 pg) could be detected when the 6E10/4G8 F(ab')-PEG$_{24}$ beads were used. The detection level achieved in this case was equivalent to that when pure amyloid β (1-28) was analyzed by the mass spectrometer. However, also in this example, the S/N ratio when the 6E10/4G8 F(ab')-PEG$_{24}$ beads were used was lower than that when pure amyloid β (1-28) was analyzed, from which it is considered that the eluate contained minute quantities of impurities.

Also among the three kinds of IgG-protein G beads, there was a difference in detection limit. Among them, the lowest level of amyloid β (1-28) (5 pg) could be detected when the 6E10/4G8 IgG-protein G beads were used. On the other hand, in Example 2, there was no difference in detection limit among the three kinds of IgG-protein G beads, but it was confirmed that the S/N ratio was highest when the 6E10/4G8 IgG-protein G beads were used. In Example 3, the probable reason why a low level of amyloid β (1-28) could be detected when the 6E10/4G8 IgG-protein G beads were used is that also when the protein G beads to which the two kinds of antibodies were bound were used, cooperative binding was achieved by the F(ab') fragments of the different antibodies.

In fact, the Non-Patent Document 2 (Proceedings of the Japan Academy, Ser. B, Physical and biological Sciences 2011; 87(9):603-16) states that the K$_D$ value of the amyloid β (1-15)-Fc6 antibody-like molecule in which PEG is not inserted into the hinge region is lower than that of amyloid β (1-15) peptide, that is, the amyloid (1-15)-Fc6 antibody-like molecule in which PEG is not inserted into the hinge region is less likely to cause dissociation of anti-amyloid β antibody than amyloid β (1-15) peptide. The Non-Patent Document 2 suggests that cooperative binding can be achieved also when the hinge region of the antibody-like molecule is the original hinge region of IgG (to which no PEG is inserted). This is suggested also by the result of SPR analysis.

In addition, the Non-Patent Document 2 also states that the K$_D$ value of the antibody-like molecule having a hinge region into which PEG is inserted is lower than that of the antibody-like molecule having a hinge region into which PEG is not inserted. The tendency that the K$_D$ value is lowered by PEG insertion is seen also in the result of this example that the amount of the trapped antigen was larger when the 6E10/4G8 F(ab')-PEG$_{24}$ beads were used than when the 6E10/4G8 IgG-protein G beads were used.

Further, according to the result of SPR analysis in the Non-Patent Document 2, the maximum binding amount (Rmax) of the amyloid β (1-15)-PEG$_{24}$-Fc6 antibody-like molecule is 40 when the Rmax of the amyloid β (1-15)-Fc6 antibody-like molecule is 34.9. The tendency that the binding amount is increased by PEG insertion is also in accordance with the result of this example.

An experiment was performed to determine whether or not substances other than target amyloid β (1-28) were adsorbed to the beads. FIG. 13 shows a mass spectrum obtained by analyzing, with a mass spectrometer, an eluate obtained by isolating and concentrating 1 pg (307 amol) of amyloid β (1-28) spiked in plasma using the 6E10/4G8 F(ab')-PEG$_{24}$ beads. As shown in FIG. 13, when the 6E10/4G8 F(ab')-PEG$_{24}$ beads were used, no peaks (S/N≥3) other than the peak of amyloid β (1-28) were detected in the range of m/z 1,500 to 5,000. From the result, it is considered that non-specific adsorption of impurities was reduced by binding of highly-hydrophilic PEG to the beads and the absence of Fc regions of the antibodies. Therefore, it can be said that the F(ab')-PEG$_{24}$ beads are excellent also in specificity.

The invention claimed is:

1. A method of trapping amyloid β comprising contacting a sample containing amyloid β (1-28) or amyloid β (1-42) with an affinity support which comprises (a) a solid support, (b) a plurality of spacers directly covalently bound to the solid support, (c) and a plurality of immunoglobulin F(ab') or F(ab) fragments comprising the F(ab') or F(ab) region of a 6E10 antibody molecule, each bound directly covalently to a polyethylene glycol spacer having a polymerization degree of 24 and wherein the interval between the spacers is 1 to 50 angstrom (Å), wherein the amyloid β has a plurality of affinity sites and at least two of the affinity sites of the amyloid β are bound by the immunoglobulin F(ab') or F(ab) fragments simultaneously such that the amyloid β (1-28) or amyloid β (1-42) is trapped by the immunoglobulin F(ab') or F(ab) fragments via cooperative binding.

2. The method of trapping amyloid β of claim 1, wherein the amyloid β (1-28) or amyloid β (1-42) exists as a multimer or aggregate of a plurality of molecules, and the plurality of affinity sites exists on each multimer or aggregate.

3. The method of trapping amyloid β (1-28) of claim 1, wherein the affinity support additionally comprises a plurality of immunoglobulin F(ab') or F(ab) fragments comprising the F(ab') or F(ab) region of a 4G8 antibody molecule, each bound directly covalently to a spacer such that two kinds of the immunoglobulin F(ab') or F(ab) fragment are bound to the support in a mixed state.

4. A method of analyzing the amyloid β (1-28) or amyloid β (1-42) trapped according to claim 1 further comprising the steps of: (1) washing the surface of the affinity support to remove substances non-specifically adsorbed to the affinity support, (2) eluting the amyloid β bound to the immunoglobulin F(ab') or F(ab) fragments from the affinity support; (3) collecting the amyloid β so eluted; and (4) analyzing the eluted amyloid β by surface plasmon resonance (SPR) or mass spectrometry.

5. The method of trapping amyloid β (1-28) or amyloid β (1-42) of claim 1, wherein the interval between the spacers is 1.5 to 30 angstrom (Å).

* * * * *